United States Patent
Finan et al.

(10) Patent No.: US 10,583,249 B2
(45) Date of Patent: Mar. 10, 2020

(54) VISUALIZATION AND ANALYSIS TOOL FOR DRUG DELIVERY SYSTEM

(71) Applicant: Animas Corporation, West Chester, PA (US)

(72) Inventors: Daniel Finan, Philadelphia, PA (US); Pavel Vereshchetin, Moscow (RU)

(73) Assignee: LifeScan IP Holdings, LLC, Malvern, PA (US)

( * ) Notice: Subject to any disclaimer, the term of this patent is extended or adjusted under 35 U.S.C. 154(b) by 532 days.

(21) Appl. No.: 15/411,117

(22) Filed: Jan. 20, 2017

(65) Prior Publication Data
US 2017/0224920 A1    Aug. 10, 2017

Related U.S. Application Data

(60) Provisional application No. 62/291,792, filed on Feb. 5, 2016.

(51) Int. Cl.
*A61M 5/172* (2006.01)
*A61M 5/142* (2006.01)
(Continued)

(52) U.S. Cl.
CPC ...... *A61M 5/1723* (2013.01); *A61M 5/14244* (2013.01); *G16H 20/17* (2018.01);
(Continued)

(58) Field of Classification Search
CPC ................ A61M 5/1723; A61M 38/28; A61M 5/14244; A61M 5/172; A61M 5/14248;
(Continued)

(56) References Cited

U.S. PATENT DOCUMENTS

| 5,251,126 A | 10/1993 | Kahn et al. |
| 7,060,059 B2 | 6/2006 | Keith et al. |

(Continued)

FOREIGN PATENT DOCUMENTS

WO    2012051344 A2    4/2012

OTHER PUBLICATIONS

Atlas et al., "MD-Logic Artificial Pancreas System," Diabetes Care, vol. 33, No. 5, May 2010.
(Continued)

*Primary Examiner* — Manuel A Mendez

(57) ABSTRACT

A visualization and analysis tool is provided for an insulin delivery system, such as an artificial pancreas, in which insulin is delivered based upon a system algorithm using a pump that is patient controllable in order to adjust insulin delivery relative to a baseline delivery rate; e.g., pre-set basal rate and a sensor for measuring glucose levels. The tool is configured with a controller of the system to detect and log events that are based on differences between actual insulin delivered by the system and the baseline delivery rate. These detected events are metrics that provide information relating to the therapeutic value of the system which, without such metrics, may be overlooked or unnoticed, thereby fostering trust and confidence in the delivery system. In addition, information is provided which may enable further improved glucose control.

9 Claims, 20 Drawing Sheets

(51) Int. Cl.
*G16H 40/67* (2018.01)
*G16H 40/63* (2018.01)
*G16H 50/70* (2018.01)
*G16H 20/17* (2018.01)

(52) U.S. Cl.
CPC ............ *G16H 40/63* (2018.01); *G16H 40/67* (2018.01); *G16H 50/70* (2018.01); *A61M 2205/3553* (2013.01); *A61M 2205/3584* (2013.01); *A61M 2205/52* (2013.01); *A61M 2230/005* (2013.01); *A61M 2230/201* (2013.01)

(58) Field of Classification Search
CPC .. A61M 5/142; A61B 5/14532; A61B 5/4839; A61B 5/7275; A61B 5/1495; G06F 19/3456; G06F 19/3468; G06F 19/3418; G01N 33/6893; G16H 50/20; G16H 20/17; G16H 50/50; G16H 40/63; C12Q 1/6883
See application file for complete search history.

(56) References Cited

U.S. PATENT DOCUMENTS

| | | | |
|---|---|---|---|
| 7,647,237 | B2 | 1/2010 | Malave et al. |
| 7,670,288 | B2 | 3/2010 | Sher |
| 8,079,955 | B2 | 12/2011 | Ward et al. |
| 8,285,487 | B2 | 10/2012 | Bergstrom et al. |
| 8,480,580 | B2 | 7/2013 | Wolpert et al. |
| 8,514,086 | B2 | 8/2013 | Harper et al. |
| 8,562,587 | B2 | 10/2013 | Kovatchev et al. |
| 8,579,815 | B2 | 11/2013 | Galley et al. |
| 8,635,046 | B2 | 1/2014 | Budiman |
| 8,706,691 | B2 | 4/2014 | McDaniel et al. |
| 8,761,940 | B2 | 6/2014 | Long et al. |
| 8,762,070 | B2 | 6/2014 | Doyle, III et al. |
| 9,262,586 | B2 | 2/2016 | Steiger et al. |
| 2008/0106431 | A1* | 5/2008 | Blomquist ........ A61M 5/14244 340/4.13 |
| 2008/0172030 | A1 | 7/2008 | Blomquist |
| 2011/0148905 | A1 | 6/2011 | Simmons et al. |
| 2011/0257627 | A1 | 10/2011 | Hovorka |
| 2011/0313680 | A1 | 12/2011 | Doyle, III et al. |
| 2013/0231642 | A1 | 9/2013 | Doyle, III et al. |
| 2013/0298063 | A1 | 11/2013 | Joy et al. |
| 2013/0338629 | A1 | 12/2013 | Agrawal et al. |
| 2014/0046159 | A1 | 2/2014 | Kovatchev et al. |
| 2014/0081236 | A1 | 3/2014 | Wilinska et al. |
| 2014/0180240 | A1 | 6/2014 | Finan et al. |
| 2014/0200559 | A1 | 7/2014 | Doyle, III et al. |
| 2014/0206970 | A1 | 7/2014 | Wesley et al. |
| 2014/0276555 | A1 | 8/2014 | Morales |
| 2014/0350369 | A1 | 11/2014 | Budiman et al. |
| 2014/0365136 | A1 | 12/2014 | Mears et al. |
| 2014/0374275 | A1 | 12/2014 | Morales et al. |
| 2015/0025495 | A1* | 1/2015 | Peyser ............... A61B 5/14532 604/504 |
| 2015/0057634 | A1* | 2/2015 | Mastrototaro ...... A61M 5/1723 604/500 |
| 2015/0100038 | A1 | 4/2015 | McCann et al. |
| 2015/0324520 | A1 | 11/2015 | Aykroyd et al. |
| 2017/0199985 | A1* | 7/2017 | Mazlish ............. A61M 5/1723 |

OTHER PUBLICATIONS

Cobelli et al., "Artificial Pancreas: Past, Present, Future," Diabetes vol. 60, Nov. 2011.

Kovatchev et al., "Control to Range for Diabetes: Functionality and Modular Architecture," Journal of Diabetes Science and Technology, vol. 3, Issue 5, Sep. 2009.

Lee et al., "A Closed-Loop Artificial Pancreas Based on MPC: Human Friendly Identification and Automatic Meal Disturbance Rejection," Proceedings of the 17th World Congress, The International Federation of Automatic Control, Seoul Korea Jul. 6-11, 2008.

Lee et al., "A Closed-Loop Artificial Pancreas Using Model Predictive Control and a Sliding Meal Size Estimator," Journal of Diabetes Science and Technology, vol. 3, Issue 5, Sep. 2009.

Magni et al., "Model Predictive Control of Type 1 Diabetes: An in Silico Trial," Journal of Diabetes Science and Technology, vol. 1, Issue 6, Nov. 2007.

Magni et al., "Run-to-Run Tuning of Model Predictive Control for Type 1 Diabetes Subjects: In Silico Trial," Journal of Diabetes Science and Technology, vol. 3, Issue 5, Sep. 2009.

Paola Soru et al., "MPC Based Artificial Pancreas; Strategies for Individualization and Meal Compensation," Annual Reviews in Control 36, p. 118-128 (2012).

Percival et al., "Closed-Loop Control and Advisory Mode Evaluation of an Artificial Pancreatic β Cell: Use of Proportional-Integral-Derivative Equivalent Model-Based Controllers," Journal of Diabetes Science and Technology, vol. 2, Issue 4, Jul. 2008.

Percival et al., "Closed-Loop Control of an Artificial Pancreatic β-Cell Using Multi-Parametric Model Predictive Control," Diabetes Research 2008.

Wang et al., "Automatic Bolus and Adaptive Basal Algorithm for the Artificial Pancreatic β-Cell," Diabetes Technology and Therapeutics, vol. 12, No. 11, 2010.

International Search Report and Written Opinion issued in related International Patent Application No. PCT/US2017/14291, dated Apr. 5, 2017, 9 pages.

\* cited by examiner

| Metric | Overall | Overnight (10pm-6am) | Sleep Care Enabled |
|---|---|---|---|
| *Overall Control* | | | |
| Time in 70-180 mg/dL range | XX.X % | XX.X % | XX.X % |
| Mean glucose | XX.X mg/dL | XX.X mg/dL | XX.X mg/dL |
| Coefficient of variation, CV | XX.X mg/dL | XX.X mg/dL | XX.X mg/dL |
| *Hypoglycemia* | | | |
| Time spent < 50 mg/dL | XX.X % | XX.X % | XX.X % |
| Time spent < 60 mg/dL | XX.X % | XX.X % | XX.X % |
| Time spent < 70 mg/dL | XX.X % | XX.X % | XX.X % |
| *Hyperglycemia* | | | |
| Time spent > 180 mg/dL | XX.X % | XX.X % | XX.X % |
| Time spent > 250 mg/dL | XX.X % | XX.X % | XX.X % |
| Time spent > 300 mg/dL | XX.X % | XX.X % | XX.X % |
| *Usage* | | | |
| CGM usage | XX.X % | XX.X % | n/a |

FIG. 17

| Metric | Overall |
|---|---|
| Total daily dose, TDD (mean) | XX.X u |
| Basal percent | XX.X % |
| Bolus percent | XX.X % |

*FIG. 18*

| Event # | Date | Time (Duration) | Total Insulin Withheld | Percent Insulin Withheld | CGM Nadir | CGM at Start of Event | CGM at End of Event |
|---|---|---|---|---|---|---|---|
| 1 | [date] | YY:YY am - YY:YY pm (X hrs, X min) | XX.X u | XX.X% | XX mg/dL | XX mg/dL | XX mg/dL |
| 2 | [date] | YY:YY am - YY:YY am (X hrs, X min) | XX.X u | XX.X% | XX mg/dL | XX mg/dL | XX mg/dL |
| ... | | | | | | | |
| N | [date] | YY:YY pm - YY:YY am (X hrs, X min) | XX.X u | XX.X% | XX mg/dL | XX mg/dL | XX mg/dL |

*FIG. 19*

| Event # | Date | Time (Duration) | Total Insulin Added | Percent Insulin Added | CGM Peak | CGM at Start of Event | CGM at End of Event |
|---|---|---|---|---|---|---|---|
| 1 | [date] | YY:YY am - YY:YY pm (X hrs, X min) | XX.X u | XX.X% | XX mg/dL | XX mg/dL | XX mg/dL |
| 2 | [date] | YY:YY am - YY:YY am (X hrs, X min) | XX.X u | XX.X% | XX mg/dL | XX mg/dL | XX mg/dL |
| ... | | | | | | | |
| N | [date] | YY:YY pm - YY:YY am (X hrs, X min) | XX.X u | XX.X% | XX mg/dL | XX mg/dL | XX mg/dL |

*FIG. 20*

VISUALIZATION AND ANALYSIS TOOL FOR DRUG DELIVERY SYSTEM

CROSS REFERENCE TO RELATED APPLICATION

This application claims priority under relevant portions of 35 U.S.C. § 119 to U.S. Application No. 62/291,792, filed Feb. 5, 2016, the entire contents of which are hereby incorporated by reference.

TECHNICAL FIELD

This invention is generally directed to the field of glucose management and more specifically to a system that delivers insulin, such as an artificial pancreas, controlled by an insulin delivery modulating algorithm, and a related method in which system responses, to changes in user's glucose, are detected. A visualization tool enables meaningful data analysis and can also be used to improve insulin therapy by supporting therapeutic decisions.

BACKGROUND

Diabetes mellitus is a chronic metabolic disorder caused by an inability of the pancreas to produce sufficient amounts of the hormone insulin. This failure leads to hyperglycemia, i.e. the presence of an excessive amount of glucose in the blood plasma. Persistent hyperglycemia has been associated with a variety of serious symptoms and life threatening long term complications. Because restoration of endogenous insulin production is not yet possible, a permanent therapy is necessary which provides constant glycemic control in order to maintain the level of blood glucose within normal limits. Such glycemic control is achieved by regularly supplying external insulin to the body of the patient.

Substantial improvements in glycemic control have been achieved by the development of drug delivery devices that allow for the delivery of drug in a manner that is similar to naturally occurring physiological processes and can be controlled to follow standard or individually modified protocols to give the patient better glycemic control.

The drug delivery devices can be constructed as implantable devices. Alternatively, an external device with an infusion set for subcutaneous infusion to the patient via the transcutaneous insertion of a catheter or cannula may be used. The external drug delivery devices are generally mounted on clothing or, and preferably, hidden beneath or inside clothing, or mounted on the body and are generally controlled via a user interface built-in to the device or on a separate remote control device.

The delivery of suitable amounts of insulin by the drug delivery device requires that the patient frequently determines his or her blood glucose level. This value is inputted into the external pumps or controller, to determine whether a suitable modification to the default or currently in-use insulin delivery protocol, i.e. dosage and timing, is needed. The determination of blood glucose concentration is typically performed by means of an episodic measuring device, such as a hand-held electronic meter, which receives blood samples via enzyme-based test strips and calculates the blood glucose value based on the enzymatic reaction.

Alternatively, a continuous glucose monitor ("CGM") may be utilized with drug delivery devices to allow for closed loop control of the insulin that is being infused into the diabetic patients. To allow for closed-loop control of the infused insulin, autonomous modulation of the drug being delivered to the user is provided by a controller using one or more algorithms. For example, a proportional-integral-derivative ("PID") controller may be utilized and can be tuned based on simple rules of metabolic models.

Alternatively, a model predictive controller ("MPC") has been demonstrated to be more robust than PID because MPC proactively considers the near future effects of control changes, sometimes subject to constraints, in determining the output of the MPC, whereas PID typically involves only past outputs in determining future changes. Constraints can be implemented in the MPC controller such that a solution is in a confined "space", meaning within imposed delivery limitations, is guaranteed and the system is prevented from exceeding a limit that has been reached.

Details of the MPC controllers, and variations on the MPC and mathematical models representing the complex interaction of glucose and insulin are shown and described in the following documents:

U.S. Pat. No. 7,060,059; U.S. Patent Application Nos. 2011/0313680, 2011/0257627, and 2014/0180240; International Publication WO 2012/051344; Percival et al., "Closed-Loop Control and Advisory Mode Evaluation of an Artificial Pancreatic β-Cell: Use of Proportional-Integral-Derivative Equivalent Model-Based Controllers," J. Diabetes Sci. Techn., Vol. 2, Issue 4, July 2008; Paola Soru et al., "*MPC Based Artificial Pancreas; Strategies for Individualization and Meal Compensation,*" Annual Reviews in Control 36, p. 118-128 (2012); Cobelli et al., "*Artificial Pancreas: Past, Present, Future,*" Diabetes, Vol. 60, November 2011; Magni et al., "*Run-to-Run Tuning of Model Predictive Control for Type 1 Diabetes Subjects: In Silico Trial,*" J. Diabetes Sci. Techn., Vol. 3, Issue 5, September 2009; Lee et al., "*A Closed-Loop Artificial Pancreas Using Model Predictive Control and a Sliding Meal Size Estimator,*" J. Diabetes Sci. Techn., Vol. 3, Issue 5, September 2009; Lee et al., "*A Closed-Loop Artificial Pancreas based on MPC: Human Friendly Identification and Automatic Meal Disturbance Rejection,*" Proceedings of the 17th World Congress, The International Federation of Automatic Control, Seoul Korea Jul. 6-11, 2008; Magni et al., "*Model Predictive Control of Type 1 Diabetes: An in Silico Trial,*" J. Diabetes Sci. Techn., Vol. 1, Issue 6, November 2007; Wang et al., "*Automatic Bolus and Adaptive Basal Algorithm for the Artificial Pancreatic β-Cell,*" Diabetes Techn. Ther., Vol. 12, No. 11, 2010; Percival et al., "*Closed-Loop Control of an Artificial Pancreatic β-Cell Using Multi-Parametric Model Predictive Control*" Diabetes Research 2008; Kovatchev et al., "*Control to Range for Diabetes: Functionality and Modular Architecture,*" J. Diabetes Sci. Techn., Vol. 3, Issue 5, September 2009; and Atlas et al., "*MD-Logic Artificial Pancreas System,*" Diabetes Care, Vol. 33, No. 5, May 2010. All articles or documents cited in this application are hereby incorporated by reference into this application as if fully set forth herein.

The advent of autonomous-dosing, artificial pancreas ("AP")-type devices in diabetes care necessarily creates data that is much more abundant and complex than that of traditional, non-AP insulin pumps. This added complexity may overwhelm users of the devices, as well as caregivers and health care practitioners ("HCPs"), especially in the absence of a suitable tool to assist in the interpretation of such data and in which the complete value of the AP dosing paradigm may be lost.

BRIEF DESCRIPTION OF THE DRAWINGS

The accompanying drawings illustrate presently preferred embodiments of the invention, and, together with the general description given above and the detailed description given below, serve to explain features of the invention.

FIG. 17 depicts a tabular representation listing various CGM sensor related metrics of an insulin delivery system over a predetermined time period.

FIG. 18 depicts a tabular representation of metrics relating to insulin delivery for a delivery system over a predetermined (daily) time period.

FIG. 19 is a tabular representation denoting hypoglycemic activity events over a predetermined time period.

FIG. 20 is a tabular representation according to one embodiment denoting hyperglycemic activity events over a predetermined time period.

DETAILED DESCRIPTION

Figure 1:
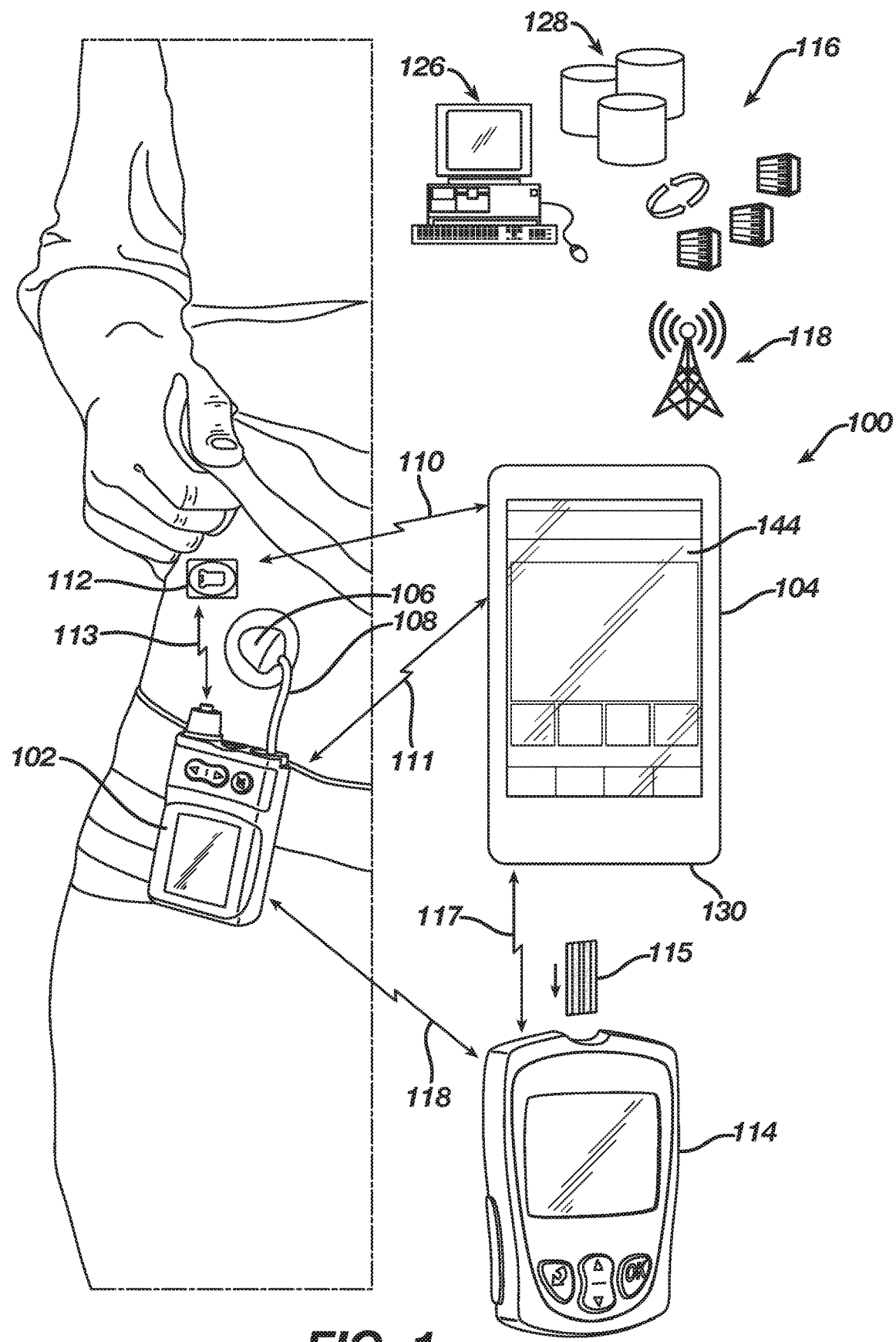
FIG. 1 illustrates aspects of a diabetic management system.

The following detailed description is to be read with reference to the drawings, in which like elements in different drawings are identically numbered. The drawings depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "patient," "host" and "user" refer to any human or animal subject and are not intended to limit the systems or methods to human use, although use of the subject invention in a human patient represents a preferred embodiment. Furthermore, the term "user" includes not only the patient using a drug infusion device but also the caretakers (e.g., parent or guardian, nursing staff or home care employee). The term "drug" may include hormones, biologically active materials, pharmaceuticals or other chemicals that cause a biological response (e.g., glycemic response) in the body of a user or patient and, preferably, is insulin.

According to one aspect, there is provided an insulin delivery system comprising a pump that is patient controllable to adjust insulin delivery rates, a sensor for measuring glucose levels, and a controller configured to deliver insulin based upon autonomous modulation. The system further comprises a visualization and analysis tool engageable with the system, the tool enabling the detection and display of at least one activity event (a metric) indicative of glycemic changes in a patient, in which the at least one activity event is based on predetermined differences between system-delivered insulin and a predetermined basal rate over time.

The system delivers insulin at periodic time intervals wherein the at least one activity event is detected based upon changes in insulin that are scheduled to be delivered by the system, as compared to actual insulin that is delivered. According to one version, if the ratio of insulin delivered as compared to actual insulin scheduled exceeds a threshold periodically as averaged over predetermined time intervals, this triggers the onset of an activity event. The activity event continues until the periodic averaging no longer exceeds the threshold. An activity event can be detected even while the patient's glucose level, as measured by the sensor, remains in an acceptable target range.

According to another aspect, there is provided a method for improving an insulin delivery system, the system comprising an insulin delivery device, at least one sensor for measuring glucose levels and a controller configured to direct the delivery of insulin by the delivery device based upon autonomous modulation, the method comprising: providing glucose data from the sensor and insulin delivery data from the delivery device over a predetermined time period to a visualization and analysis tool; and detecting and displaying at least one activity event based on predetermined differences between insulin delivered by the system based on a delivery algorithm used by the controller and a predetermined basal rate used by the pump.

In this regard and according to one version, Applicants have devised a metric that quantitatively captures instances when an insulin delivery modulating AP algorithm (e.g., utilizing MPC) takes significant insulin-modulating action to avoid or mitigate potential hypo-glycemic and hyperglycemic excursions of the system user's blood glucose. The value that is created by viewing and understanding such a metric has at least two (2) components. First, retrospective analysis by the patient, caregiver or HCP of the metric can elucidate instances in recent history of the patient in which the system (algorithm) took significant action and evidently avoided a breach of either the user's low or high glucose threshold, keeping the patient safe and simultaneously pre-empting both an annoying alarm and a self-treatment by the user. This understanding is essential for the user and care-givers in fostering trust in the system.

Second, identified patterns in the metric, over time, can uncover therapeutic insights that can lead to more improved glucose control. For example, the user may see that the metric captures the same kind of event during each overnight period over a predetermined time (e.g., a week). Using this information, the user or the HCP can fine-tune the basal rate during the overnight period and thereby obtain even better glucose control in the succeeding weeks and months following the adjustment. A metric herein devised is referred to herein as an artificial pancreas activity event ("APAE"). The purpose of this metric is to capture and describe highlights to the user, in a simplified way, of the value imparted by the system algorithm in adding to the user's diabetic care. For discussions herein the metric can have two analogous variations; namely, Hypo-APAEs and Hyper-APAEs.

APAEs can be derived from calculations based upon sampling at predetermined and periodic time intervals. According to one version, three (3) sample averages are obtained, in which each sampling interval can be, for example, five (5) minutes. As a result, the APAEs can be derived according to this described sampling interval based on consecutive 15 minute averages of the patient-scheduled insulin delivery amount (e.g., basal amount) and consecutive 15 minute averages of the system's actual delivered insulin, as determined by the system's AP algorithm.

According to one version, a Hypo-APAE is detected if for at least two consecutive 15 minute averages, the system-delivered insulin is at least X times lower than (that is, less than $(1/X)*100\%$ of) the corresponding 15-minute averages of the patient-scheduled delivery amount (inclusive of temporary basal and combination/extended bolus programs, but not one-time boluses). For example and if X=1.5, then $(1/X*100\%=67\%)$. In this example and once detected, the Hypo-APAE does not stop being logged and displayed until the condition is no longer satisfied for at least two (2) consecutive 15-minute averages.

Similarly, a Hyper-APAE can be detected if, for at least two consecutive 15-minute averages, the system-commanded insulin is at least Y times higher than (that is, greater than $Y*100\%$ of) the corresponding 15 minute averages of the patient-scheduled delivery amount (inclusive of temporary basal and combination/extended bolus programs, but not one time boluses). For purposes of this example and if Y=1.5, then $Y*100\%=150\%$. Once detected, the Hyper-APAE does not stop being logged and displayed until the condition is no longer satisfied for at least two consecutive 15 minute averages.

Using a visualization and analysis tool as described herein, a dataset over a predetermined period of time (e.g., one week) can be presented to the user detailing insulin delivery data in which Hypo-APAEs and Hyper-APAEs can be detected and displayed for the user, as aligned with sensor (i.e. CGM) data.

The visualization and analysis tool can facilitate the analysis of the obtained data and the calculated metric. For example and according to one version, a landscape plot can be created in which time of day over an extended period can be depicted, assessing the system's action aligned with time of day over that total period. This landscaping enables patients and HCPs to fine-tune aspects of the insulin delivery system, such as pump settings and basal rates, to further improve glucose control. Alternatively, various metrics including APAEs can be provided to the user or HCP in tabular format.

Advantageously, the user becomes aware that the closed loop AP system is silently, autonomously keeping the patient safe from hypoglycemia and hyperglycemia, providing added trust in the system. Furthermore, the user can glean insights from the system created data, whether graphical or tabular, using the herein described visualization tool that lead to making therapeutic adjustments (e.g., basal rate adjustments) that may further improve long term glycemic control.

A further related advantage is that in instances when the closed loop system has failed to prevent a hypo- or hyperglycemic excursion and, thus, failed to avoid the associated alarm, but was acting significantly on the user's behalf before such an alarm, the user becomes aware that the system has effectively mitigated the excursion in terms of its severity, duration or time of onset.

According to at least one aspect, the following discussion relates to a metric for determining activity events relating to insulin control for an artificial pancreas and a visualization and analysis tool for performing meta-analysis based on the use of the metric. In terms of which kind of algorithms this metric and visualization and analysis tool can be applied to, the tool can work with any data produced by literally any AP (control) algorithm that autonomously modulates insulin relative to the patient-set basal rate. Therefore and while the examples herein described relate to a system that employs MPC, the invention can be applied to any insulin delivery system employing any form of continuous autonomous modulation (PID and the like), regardless of the type of algorithm employed thereby.

In addition, the system is applicable to more than one preset basal rate per 24 hours. By way of one example, a patient may set (3) three different basal rates throughout the day: e.g., one basal rate for the night, another basal rate for the day, and another basal rate for the time of exercise in the afternoon. A known basal rate profile (which may be part of the therapy that is assigned by the patient's HCP) can be programmed in the insulin delivery pump by the patient and thus is known, and the output of the algorithm—the modified rate of delivery, including the times when the modification is "zero"—that is, the preset basal rate is not changed is also known. These parameters can each be used for the development of the metric, as herein described in greater detail.

FIG. 1 illustrates aspects of a drug (insulin) delivery system 100. The drug delivery system 100 includes a drug delivery device 102, such as an infusion pump and a controller 104. The drug delivery device 102 can be connected to an infusion set 106 via flexible tubing 108.

The drug delivery device 102, as depicted, is configured to transmit and receive data to and from the remote controller 104 by, for example, radio frequency ("RF") or Bluetooth® Low Energy ("BLE") communication 111. The delivery device 102 is also configured to wirelessly receive glucose data from a CGM sensor 112 through a wireless communication channel (e.g., BLE) 110. Alternatively, the drug delivery device 102 may also function as a stand-alone device having its own built-in controller. In one embodiment, the drug delivery device 102 can be an insulin infusion device and the controller 104 can be a hand-held portable controller device or a consumer electronic device, such as a smart phone, exercise or user monitoring device, or the like. In such an embodiment, data transmitted from the drug delivery device 102 to a controller 104 may include information such as, but not limited to, insulin delivery data, blood glucose information, basal, bolus, insulin to carbohydrates ratio ("I:C") and insulin sensitivity factor ("ISF"). Alternatively, the glucose data from the glucose sensor 112 can be transmitted directly to the controller 104 through a wireless communication channel 110. The controller 104 can be configured to include an MPC controller. Alternatively and as shown schematically in FIG. 2, the MPC controller 224 may be integrated within a drug delivery device 200.

The control (AP) algorithm can reside in the remote controller 104, in the drug delivery device 102, or both in the configurations shown in FIG. 1. In one configuration, the controller 104 will wirelessly gather the necessary information (e.g., insulin history) from the drug delivery device 102, as well as from the glucose sensor 112 (e.g., glucose data) to allow the drug delivery device 102, using the control algorithm, to calculate the amount of insulin to be modulatively delivered by the drug delivery device 102. Alternatively, the controller 104 includes the control algorithm and may perform basal dosing or bolus calculation, sending the results of such calculations along with delivery instructions to the drug delivery device 102. In an alternative embodiment, an episodic blood glucose meter 114 and biosensors 115 also may be used alone or in conjunction with the CGM sensor 112 to provide blood glucose data to either or both of the controller 104 and the drug delivery device 102. Alternatively, the remote controller 104 may be combined with the meter 114 into either: (a) an integrated monolithic device; or (b) two separable devices that are dockable with each other to form an integrated device. Each of the devices 102, 104, and 114 has a suitable micro-controller (not shown for brevity) programmed to carry out various functionalities.

The drug delivery device 102 may also be configured for bi-directional wireless communication with a remote health monitoring station 116 through, for example, a wireless communication network 118. Remote controller 104 and remote monitoring station 116 may be configured for bi-directional wired communication through, for example, a telephone land based communication network. Remote monitoring station 116 may be used, for example, to download upgraded software to drug delivery device 102 and to process information from the drug delivery device 102. Examples of remote monitoring stations 116 may include, but are not limited to, a personal or networked computer 126, a server 128 to a memory storage, a personal digital assistant, other mobile telephone, a hospital base monitoring station or a dedicated remote clinical monitoring station. Alternatively and though not shown in FIG. 1, storage, for example, the control algorithm, may further be provided in the cloud.

Drug delivery device 102 includes processing electronics: including a central processing unit and memory elements for storing control programs and operation data, a radio frequency module, Bluetooth interface or the like for sending and receiving communication signals (i.e., messages), a display for providing operational information to the user, a plurality of navigational buttons for the user to input information, a battery for providing power to the system, an alarm (e.g., visual, auditory or tactile) for providing feedback to the user, a vibrator for providing feedback to the user, a drug delivery mechanism (e.g., a drug pump and drive mechanism) for forcing a predetermined quantity of insulin from an insulin reservoir (e.g., an insulin cartridge) through a side port connected to an infusion set 108/106 and into the body of the user. An example of a drug delivery device is in the form of a modified Animas® Vibe® insulin pump manufactured by Animas Corporation, Wayne, Pa.

User glucose levels or concentrations can be determined by the use of the CGM sensor 112. The CGM sensor 112 utilizes any known sensor technology capable of measuring glucose via CGM as, for example, using an amperometric chemical sensor with three electrodes operably connected to the sensor electronics and covered by a sensing membrane and a biointerface membrane.

The top ends of the electrodes are in contact with an electrolyte phase (not shown), which is a free-flowing fluid phase disposed between the sensing membrane and the electrodes. The sensing membrane may include an enzyme, e.g., glucose oxidase, which covers the electrolyte phase. In this exemplary sensor, the counter electrode is provided to balance the current generated by the species being measured at the working electrode. In the case of a glucose oxidase based glucose sensor, the species being measured at the working electrode is $H_2O_2$. The current that is produced at the working electrode (and flows through the circuitry to the counter electrode) is proportional to the diffusional flux of $H_2O_2$. Accordingly, a raw signal may be produced that is representative of the concentration of glucose in the user's body, and therefore may be utilized to estimate a meaningful glucose value. Details of the sensor useful in the system and associated components are shown and described in U.S. Pat. No. 7,276,029, which is incorporated by reference herein as if fully set forth herein this application. In one embodiment, a commercially available continuous glucose sensor, for example a Dexcom, Inc. G4® or G5® sensor can be utilized with the exemplary embodiments described herein.

In one embodiment of the invention, the following components can be utilized as a system for management of diabetes that is akin to an artificial pancreas: an infusion pump; an episodic glucose sensor; a continuous glucose monitor, such as those manufactured by Dexcom, Inc. with interface to connect these components and programmed in MATLAB® language or embedded code and accessory hardware to connect the components together; and at least one control algorithm that automatically regulates the rate of insulin delivery based on the glucose level of the patient, historical glucose measurement and insulin deliveries, anticipated future glucose trends, as well as patient specific information.

Figure 2:
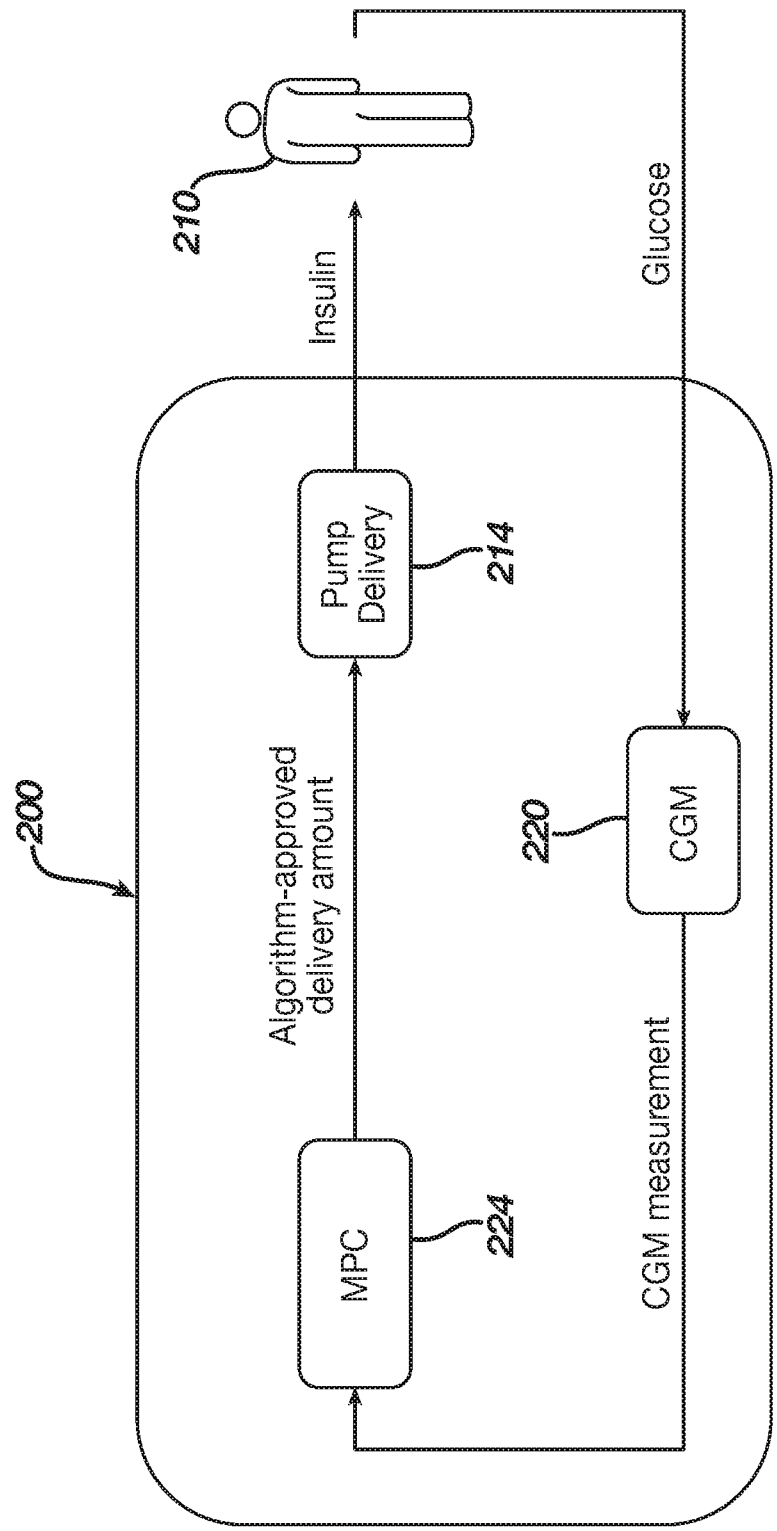
FIG. 2 illustrates a selected embodiment of a diabetic management system in schematic form.

Referring to FIG. 2, there is shown another exemplary embodiment of a drug delivery device 200, shown schematically for use in conjunction with a patient 210. The drug delivery device 200 according to this embodiment houses a pump delivery module 214, CGM module 220 and an MPC module 224. Preferably, this embodiment employs a hypoglycemia-hyperglycemia minimizer ("HHM") systems, for example, disclosed in U.S. Pat. No. 8,526,587 and U.S. patent application Ser. No. 14/015,831, both of which are incorporated in their entireties herein by reference, each being integrated within the housing of the drug delivery device 200. The CGM module 220 is configured for receiving signals from a CGM sensor 112, placed on the patient 210. As shown, the MPC module 224 is operatively connected to the CGM module 220 as well as the pump delivery module 214 and is configured to receive subcutaneous glucose information for providing the same to a stored algorithm, which is also made aware of all previous deliveries of insulin. This data is used to calculate near-future predictions of glucose levels and produce an insulin delivery rate that would mitigate the near-future predicted, or actual, hyper or hypo-glycemic conditions. The rate is then actuated by the pump delivery module 214 relative to the patient set rate corresponding to the current (e.g., 5 minute) interval. This protocol is repeated for each subsequent time interval.

Exemplary algorithms for use in the MPC module 224 are detailed in U.S. Pat. Nos. 8,562,587 and 8,762,070 and U.S. application Ser. Nos. 13/854,963 and 14/154,241, the entire contents of which are herein incorporated by reference, creating predictive values for controlling the delivery of insulin based on basal rate, meal activities and continuous glucose monitoring. Technically, CGM is conducted according to a periodic schedule (e.g., once each five minutes). As noted above, insulin is delivered to the patient 210 in this embodiment and for all following portions of this discussion using the HHM system. However and as noted previously, other known MPC or PID type delivery systems and predictive algorithms employed thereby can be utilized.

According to one embodiment, a visualization and analysis tool can be provided at the remote monitoring system 116, FIG. 1, in which relevant data from the CGM module 220 and the MPC module 224 can be wirelessly communicated, such as through the remote controller 104 as an intermediate device. Alternatively, at least aspects of the visualization tool can be provided on the drug delivery device 102, 200, or the remote controller 104, FIGS. 1 and 2, to enable viewing by a user or HCP.

For purposes of the following description, a metric has been developed for use in an insulin delivery or glucose management system. This metric is herein referred to as an APAE. In the herein described example, APAEs are derived from calculations based on three (3) sample averages in which each sampling interval is five (5) minutes in accordance with those of the HEIM delivery system. That is, the APAEs are derived based on the two most recent 15 minutes of the patient-scheduled insulin delivery amount (e.g., basal) and the two most recent 15 minutes of the system's actual delivered insulin, as determined by the AP (HEIM system) algorithm.

As will be discussed in greater detail below, the occurrence of an APAE is not fixed in terms of time, but rather is a phenomenon having a variable time period. As will be seen in the following discussion and based upon the above sampling intervals, an APAE can be 30 minutes in duration or can extend over several hours, depending on whether conditions for its detection are satisfied.

As typified by hypoglycemia and hyperglycemia, there are two types of APAEs, namely Hypo-APAEs and Hyper-APAEs used as metrics for visualization and analysis purposes. For purposes of this discussion, a Hypo-APAE is detected if for at least two (2) consecutive 15-minute averages, the system—delivered insulin is at least X times lower than the corresponding 15-minute averages of the patient-scheduled delivery amount. More specifically, detection of a Hypo-APAE occurs if the system-delivered insulin is less than (1/X)*100% of the corresponding 15-minute averages of the patient-scheduled delivery amount (inclusive of temporary basal and combination/extended bolus programs, but not one-time boluses). For purposes of the above example and if X=1.5, then (1/X)*100%=67%.

As noted, and once a Hypo-APAE is detected based on the above relation, this event will continue to be logged (and depicted using the visualization and analysis tool) until the above condition is not satisfied for at least two consecutive 15 minute averages.

Similarly and according to the following examples, a Hyper-APAE is detected if for at least two (2) consecutive 15 minute averages, the system-delivered insulin is at least Y times higher than the corresponding 15 minute averages of the patient-scheduled delivery amount. More specifically, detection of a Hyper-APAE occurs if the system-delivered insulin is greater than Y*100% of the corresponding 15 minute averages of the patient-scheduled delivery amount (inclusive of temporary basal and combination/extended bolus programs, but not one time boluses). For purposes of the above example and if Y=1.5, then Y*100%=150%.

As in the case of the Hypo-APAE, a Hyper-APAE will continue to be logged (and depicted using the visualization tool) until the above condition is not satisfied for at least two consecutive 15-minute averages. As a result and for purposes of this described embodiment, the minimum duration of an APAE (Hypo or Hyper) is 30 minutes.

Figure 3:
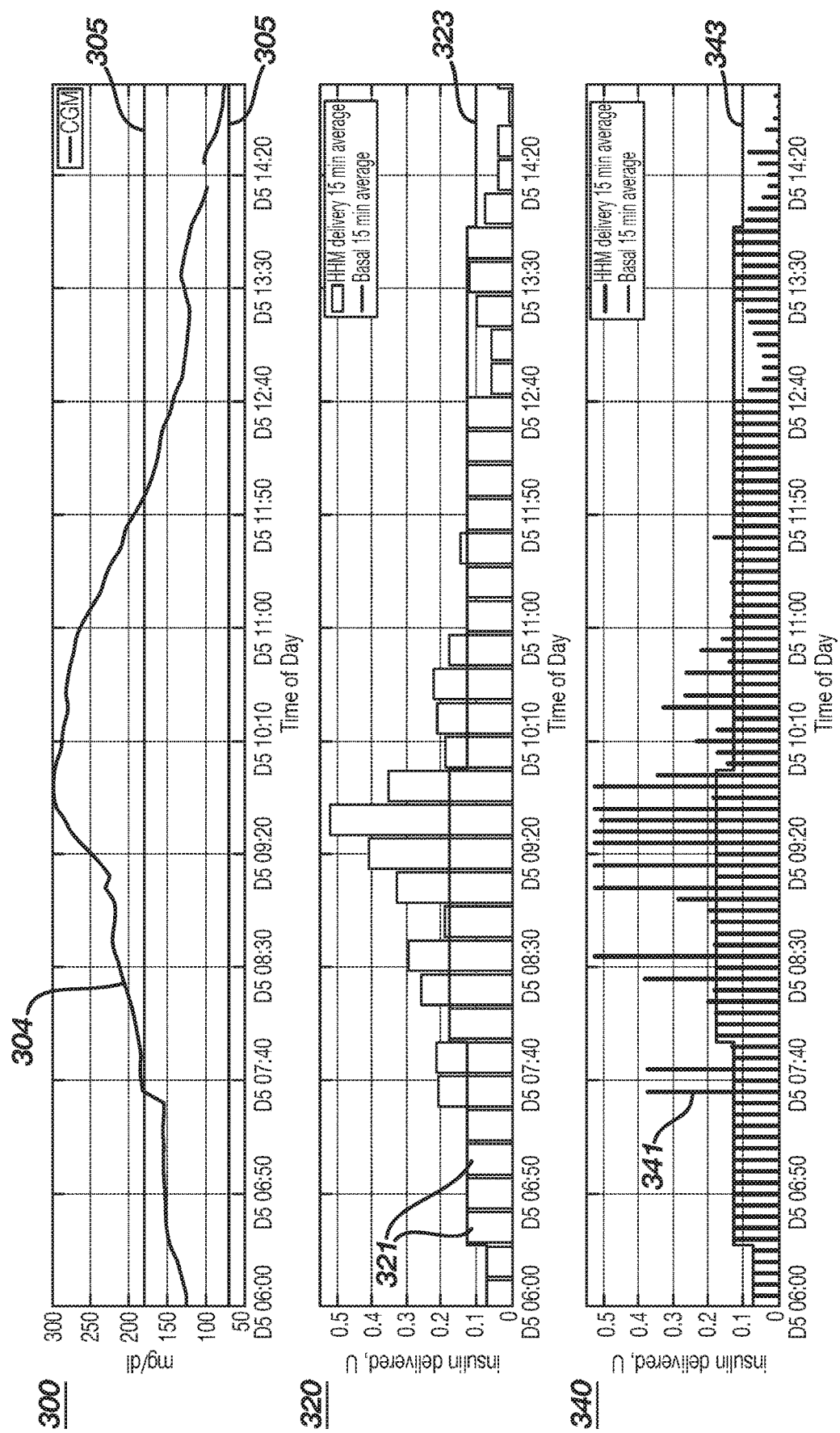
FIG. 3 depicts excerpt graphical plots from a visualization and analysis tool representing CGM and aligned insulin delivery history for a time of day covering a predetermined period.
Figure 4:
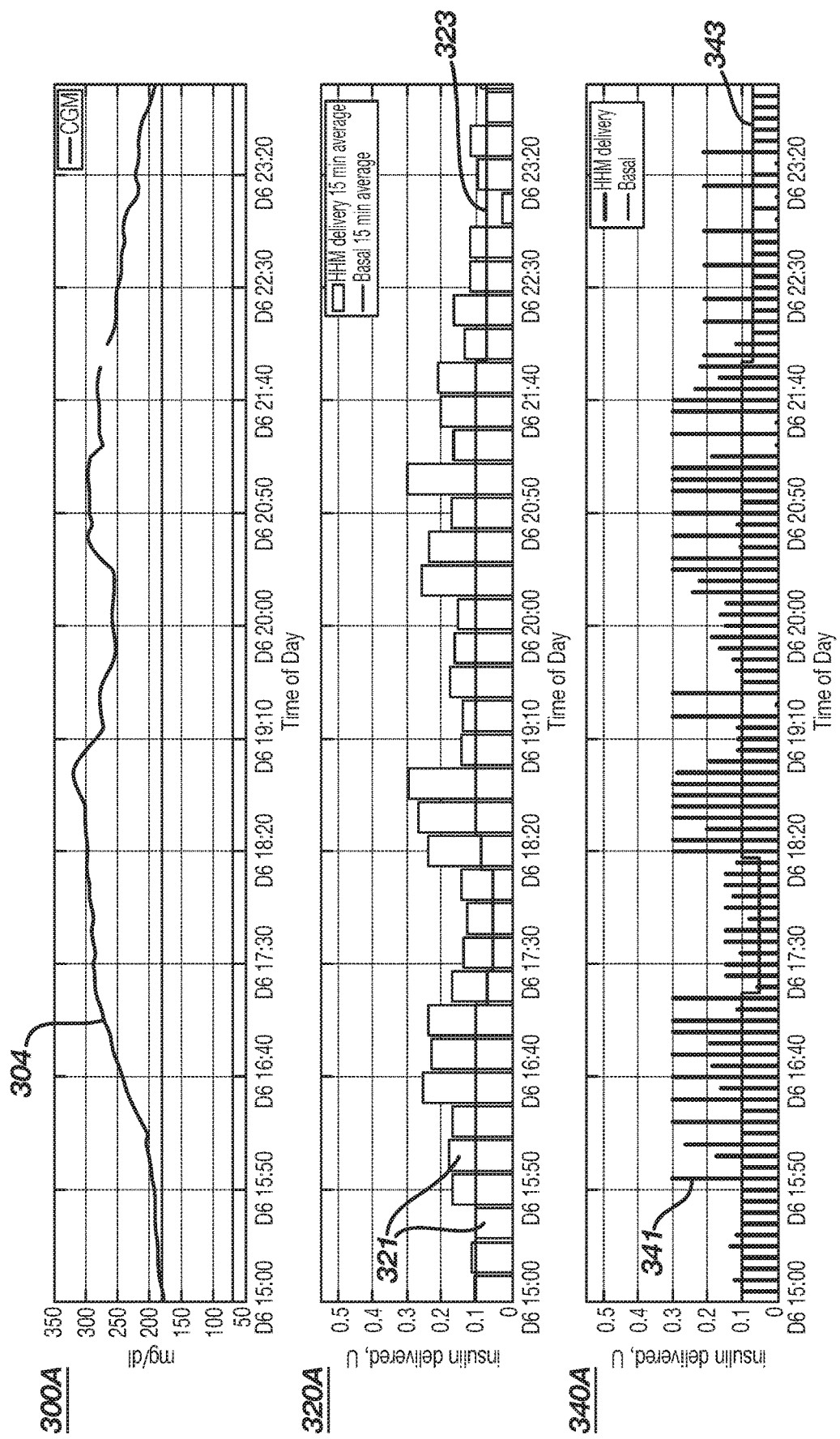
FIG. 4 depicts excerpt graphical plots from the visualization and analysis tool depicting CGM and aligned insulin delivery history covering a different predetermined time period than that depicted in FIG. 3.

Illustratively, and referring to FIGS. 3 and 4, excerpts from an illustrative seven-day dataset are provided as three (3) aligned plots 300, 300A, 320, 320A, 340, 340A using the visualization and analysis tool. This visualization and analysis tool enables an easy comparison between actual, discrete system-delivered amounts of insulin, corresponding to the 15-minute averages as aligned with CGM measured data. The x-axis of each plot commonly defines the x-axis based on a time of day. For purposes of the two figures, a continuous nine (9) hour period is provided in which FIG. 3 depicts a timeline from 06:00 to 15:00 for a specific day (Day 5 according to this example) and FIG. 4 depicts a timeline from 15:00 (Day 6) to 00:00 (Day 7). The uppermost plot 300, 300A in each figure depicts a trace of CGM blood glucose data 304, as measured in milligrams per deciliter (mg/dl) with the desired glucose range being indicated by the black horizontal lines 305 of a low limit of 70 mg/dl and a high limit of 180 mg/dl. Though the trace 304 is shown as continuous, it is in fact based upon periodic readings (e.g., each five minutes). The middle plot 320, 320A indicates 15 minute averages of insulin delivery, shown as shaded bars 321 in which each of the sample averages are situated starting on the quarters of the hour. That is, a set of samples is used calculate the corresponding averages will be located in the following hourly ranges; namely: {00 min to <15 min}, {15 min to <30 min}, {30 min to <45 min} and {45 min to <60 min}. This ensures that the borders of the 15-minute averages align with basal profile changes (which typically can be scheduled only on the halves of the hour). The horizontal black line 323 depicts scheduled basal delivery with the shaded bars 321 representing the 15 minute averages of system-delivered insulin based on the HEIM system (AP) algorithm. Finally, the lowermost (bottom) plot 340, 340A depicts the actual insulin deliveries that are actuated each five (5) minutes in accordance with the delivery system, showing the deliveries as vertical lines 341 that are used to calculate the averages in the middle plot 320, 320A along with the scheduled basal, also represented similarly in the bottom plot as the horizontal black line trace 343. In FIG. 3, the black lines 323, 343 of the middle and lowermost plots 320, 340 are identical because no temporary basal rate or extended part of a combination bolus is present though the basal rate changes at Day 5, 06:30, Day 5 08:00, Day 5 10:00 and Day, 14:00 and thus is steady when each average is calculated. A temporary basal rate can, however, be set by the patient starting at any five (5) minute step. This is more clearly shown by example in FIG. 4, in which a temporary basal rate of −50% (as shown in the bottom plot 340A) is initiated asynchronous with the quarter hour (Day 6, 17:20-Day 6, 18:20). This results in the corresponding shaded 15 minute averages 321A of the middle plot 320A showing an intermediate value near the start time and the stop time of the temporary basal rate. As in the preceding, no combination bolus is present. In this example set of figures, missed CGM data points are seen at Day 5, 14:20 and Day 6, 22:00 in FIGS. 3 and 4, respectively.

Figure 5:
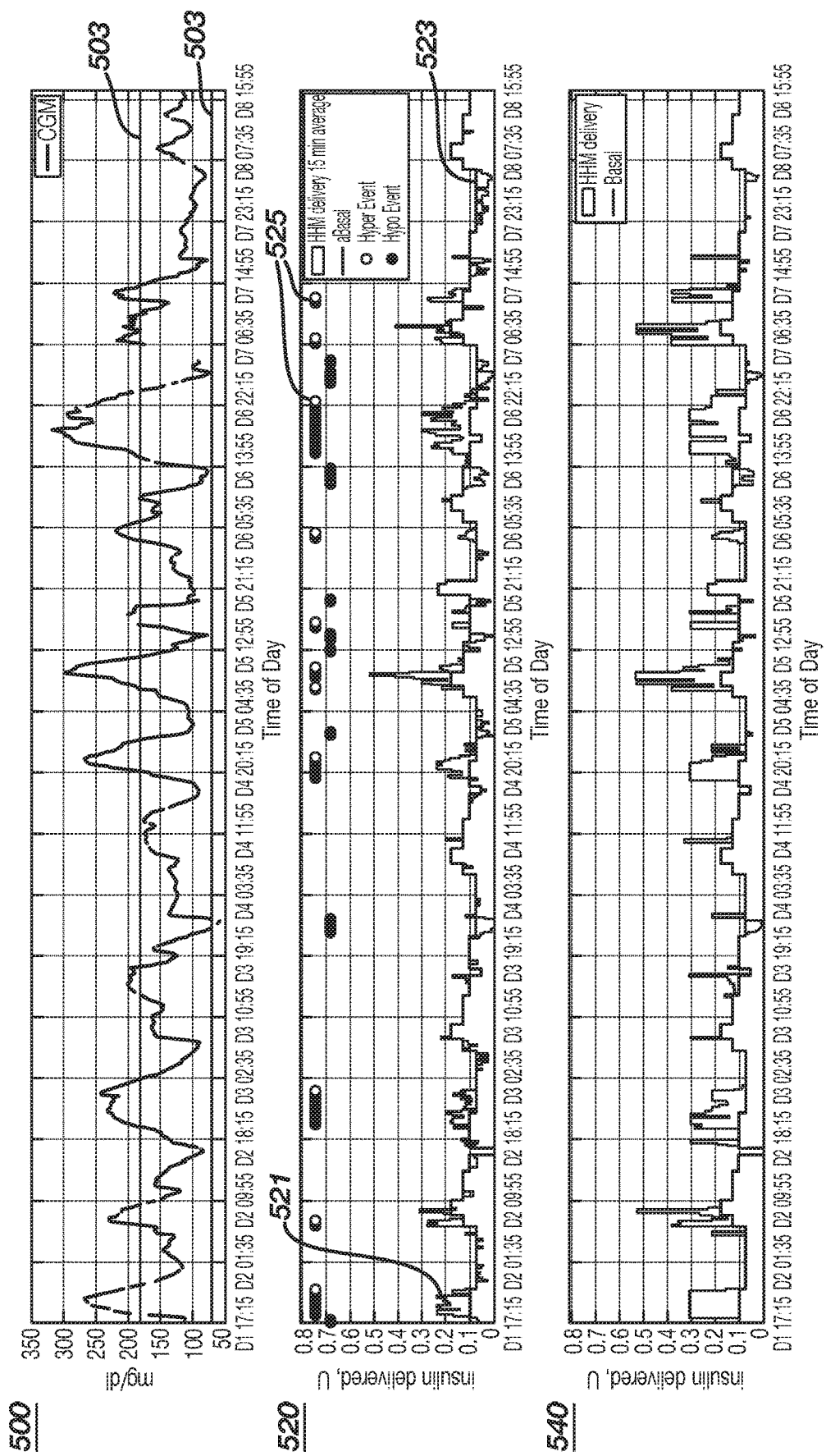
FIG. 5 depicts excerpt graphical plots of the visualization and analysis tool depicting CGM and aligned insulin delivery data over an extended period of time (7 days) and in which associated metrics (APAEs) are displayed in distinguishing fashion.

With reference to FIG. 5, an entire seven (7) day dataset is depicted in which the uppermost (top) plot 500 again provides a representation of CGM (glucose) data over the entire seven (7) day period, as measured in mg/dl, that is superimposed onto a range (70-180 mg/dl) over the time of day, the range being shown by horizontal lines 503. The two lower plots 520, 540 are aligned in terms of time of day with the top plot 500 in which the middle plot 520 provides the 15 minute averages of insulin delivery (shaded bars 521) and the black piecewise horizontal line 523 depicts scheduled basal delivery. The upper portion of this plot 520 indicates the presence of Hypo-APAE and Hyper-APAE events 525, shown away from the charted data, in which the above metrics are detected based on the above-noted activity conditions based on differentiations in the 15 minute averages between the delivered insulin amount and the patient-scheduled amounts of insulin. The events 525 are shown directly above the delivery time periods on which they were detected.

Figure 6:
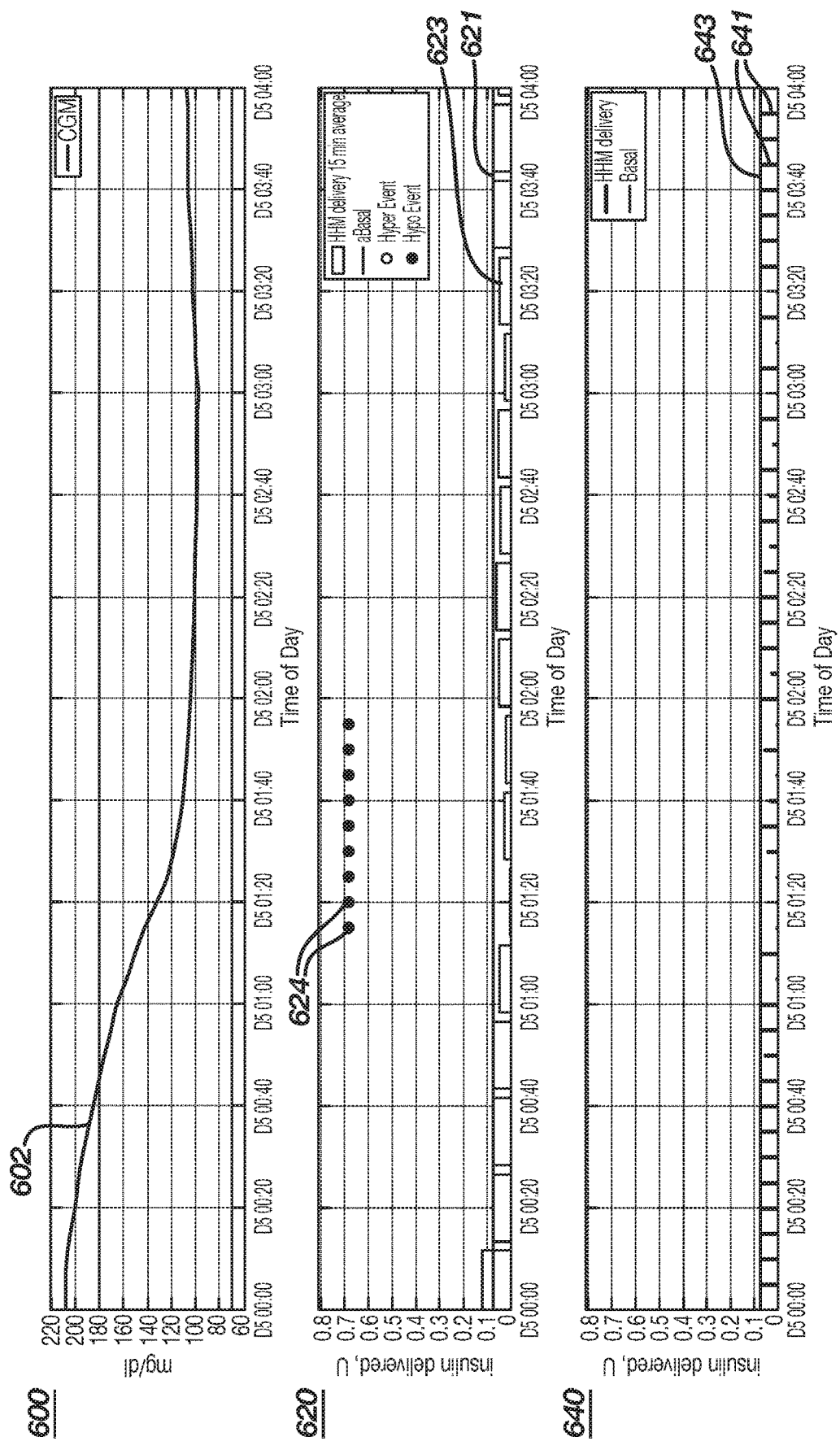
FIG. 6 represents a graphical depiction using the visualization and analysis tool of a specific metric (i.e., Hypo-APAE).
Figure 7:
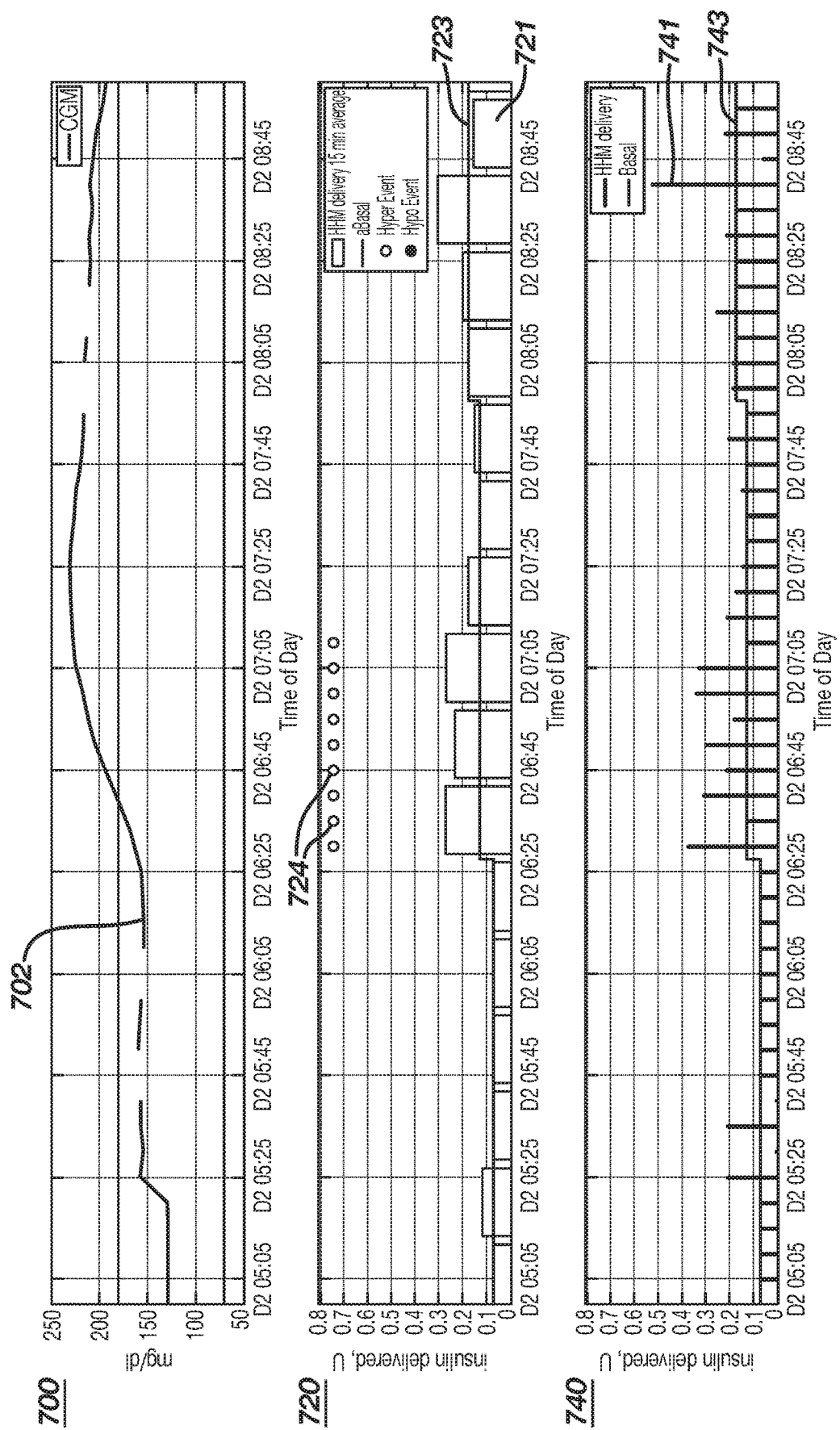
FIG. 7 represents a graphical depiction using the visualization and analysis tool of another specific metric (i.e., Hyper-APAE).

With reference to FIGS. 6 and 7, examples of Hypo-APAE and Hyper-APAEs, respectively, are shown in greater detail based on portions of the data set of FIG. 5. With specific reference to FIG. 6, the graphical representations provided are similar to those of FIGS. 3 and 4 with the uppermost plot (top) plot 600 representing CGM (glucose) data in mg/dl (shown as trace 602) over a four (4) hour span during Day 5 (00:00)-Day 5 (04:00) with 15-minute delivery averages of system-delivered insulin (shaded bars 621) and scheduled basal delivery (black line 623) being depicted in the middle plot 620 and the actual five minute incremented system deliveries (vertical lines 641) and basal delivery (horizontal line 643) being depicted in the bottom plot 640. As seen, a Hypo-APAE 624 is detected meaning that the two most recent consecutive 15 minute averages (Day 5, 3 samples of 1:15, 1:20, 1:25, inclusive, and Day 5, 3 samples of 1:30, 1:35, 1:40, inclusive) satisfied the above-noted condition for X=1.5, meaning that the averages were less than 67 percent of the scheduled insulin delivery. More specifically and in this specific event, the HHM system delivered 21 percent of the patient scheduled amount of insulin (0.13 U delivered by the HEIM vs. 0.63 U that was originally scheduled as the basal delivery). The Hypo-APAE 624 continued to be logged until two consecutive 15-minute averages (Day 5, 3 samples of 2:00, 2:05, 2:10, inclusive and Day 5, 3 samples of 2:15, 2:20, 2:25, inclusive) did not satisfy the above condition. This visualization tool enables one to see that three (3) 15 minute bars are significantly (more than 1.5 times) lower than the corresponding 15 minute averages of patient-scheduled basal delivery, as shown by the black horizontal lines on the middle plot 620. It should be further noted that certain other displayed data did not satisfy the Hypo-APAE condition of two consecutive 15 minute averages being more than 1.5 times lower than the scheduled rate. For the three deliveries at Day 5 03:00, 03:05 and 03:10, the shaded average is clearly less than 67 percent of basal (black line level). However and because the subsequent 15 minute interval does not satisfy the needed condition, there is no APAE logged.

FIG. 7 illustrates a displayed example of a Hyper-APAE event from the same data set, but over a different time period. In this example, the uppermost plot 700 again illustrates a CGM (glucose) data trace 702, as measured in mg/dl over a time of day period extending from Day 2, 5:00 to Day 5, 9:00. The middle plot 720 depicts scheduled insulin delivery over that same period (black horizontal line 723) as well as system delivered insulin (shaded areas 721) as determined in 15 minute averages. As in the preceding example, the bottommost (lower) plot 740 indicates the specific delivery events at five (5) minute intervals, including scheduled basal delivery (horizontal line 743) and system-delivered insulin, represented as vertical lines 741. As shown in the middle plot 720, at least two consecutive 15 minute averages (Day 2, 6 samples of 06:30-06:55, inclusive) satisfy the condition in which the system-delivered insulin is greater than Y*100% of the corresponding 15 minute averages of the patient-scheduled delivery amount (inclusive of temporary basal and combination/extended bolus programs, but not one time boluses) in which Y=1.5 and the delivered amount is at least 150 percent of the scheduled amount. More specifically and during this event, the HHM system delivered 206% of that originally scheduled by the patient over this time period (i.e., 2.32 U HEIM (system) vs. 1.13 U (basal). As previously noted and in order for the event to no longer be logged, at least two consecutive 15 minute averages must not satisfy the defined condition. As noted, this visualization tool enables one to see in the middle plot 720 that three (3) 15 minute shaded bars 721 are significantly higher than the corresponding 15 minute averages of patient scheduled basal. As can be gleaned from the foregoing discussion, an activity event (APAE) can be detected while the patient's glucose level is still well within the acceptable target range.

FIG. 7 also clearly illustrates an instance of a "would-be Hyper-APAE" that did not satisfy the consecutiveness condition. At Day 2, three deliveries at 08:30, 08:35 and 08:40 clearly create an average as shown in the shaded bar 721 in the middle plot 720 of greater than 150 percent of the basal (black line 723) level. However, the subsequent 15 minute interval does not satisfy the condition and therefore, no Hyper-APAE is logged.

Figure 8:
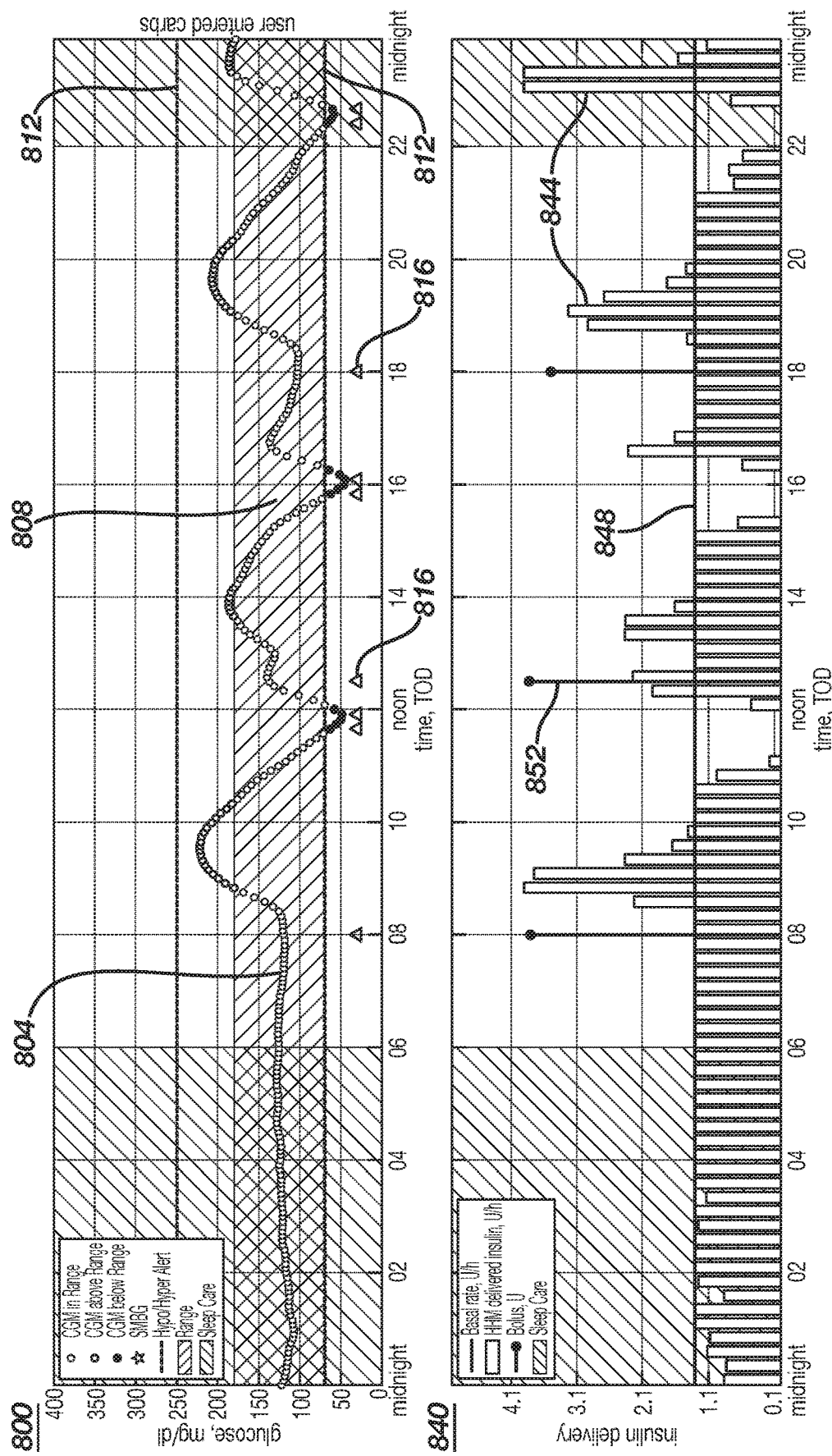
FIG. 8 represents a graphical depiction using the visualization and analysis tool of a 24 hour period in which insulin delivery is aligned with CGM data.

Referring to FIGS. 8-14, there is provided additional graphical representations using the visualization tool as based on the above defined metrics (i.e., Hypo-APAE and Hyper-APAE). FIG. 8 provides a representation taken over a 24 hour period (midnight to midnight) of insulin data in which the uppermost (top) plot 800 depicts CGM data represented by the trace 804, but in which portions of the data are illustrated based on the specific data points and not a smoothed curve output. The target range, including a low limit of 70 mg/dl and an upper limit of 180 mg/dl, is shown in the center shaded portion 808 with lower and upper limit (alert) thresholds being indicated at 50 mg/dl and 250 mg/dl, respectively, as depicted by the dashed horizontal lines 812. In this representation, carbohydrate events such as meals and hypotreatments (as tagged by a user of the system) are shown by the triangular marks 816 along the defined timeline (x-axis). The lower (bottom) plot 840 depicts insulin delivery aligned with the CGM data over the same 24 hour timeline and in which the shaded bars 844 depict 15 minute averages (as taken from three (3) five minute sampling intervals) of system delivered insulin. The horizontal black line 848 in the bottom plot 840 represents the scheduled basal rate with each of the vertical lines 852 depicting one time boluses, each measured in units ("U") of glucose.

Figure 9:
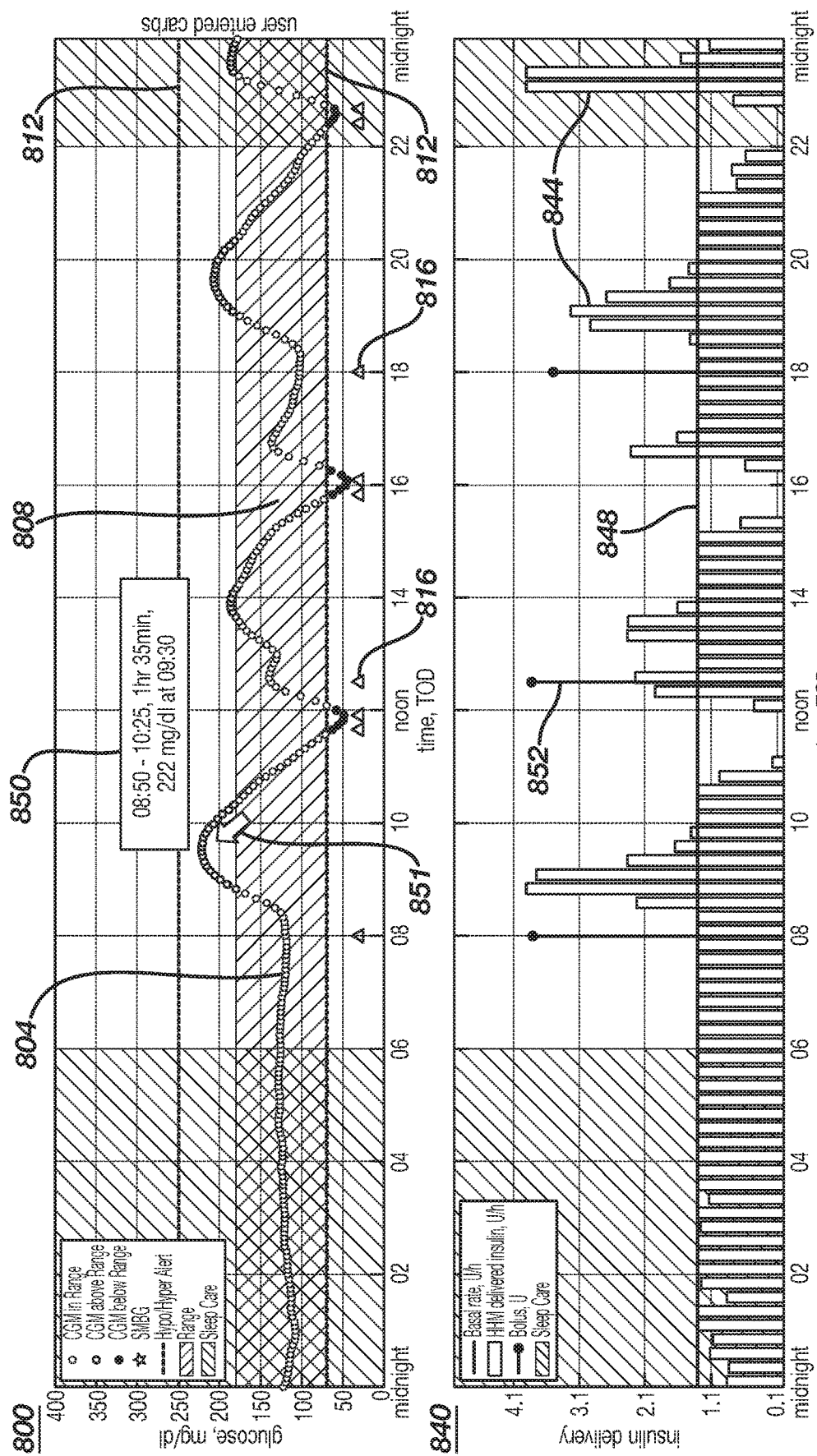
FIGS. 9 and 10 represent the graphical depictions using the visualization and analysis tool of the 24 hour plot of FIG. 8, in which statistics relating to an above the range excursion and a below the range excursion, respectively, are displayed.
Figure 10:
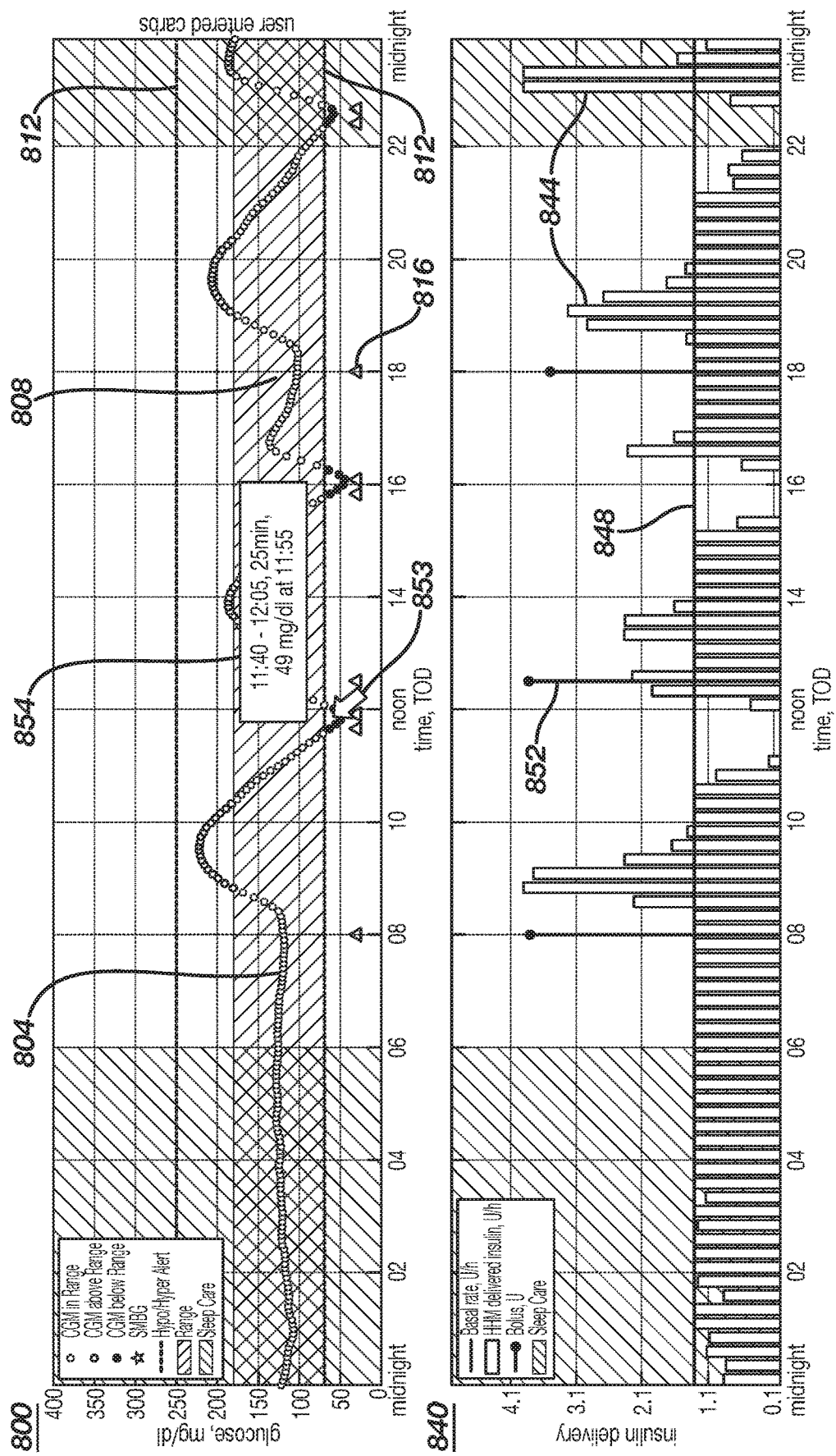
Figure 11:
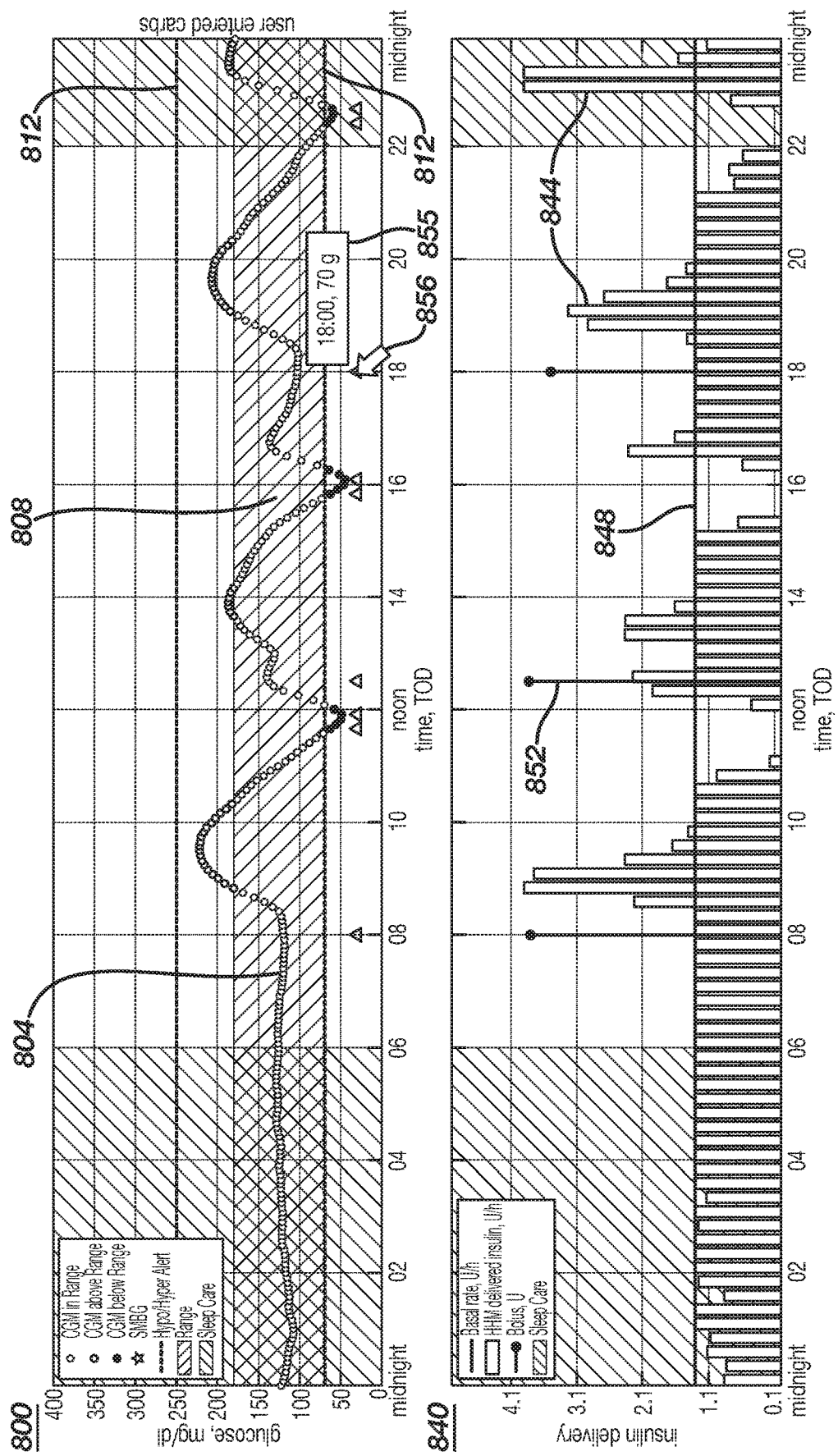
FIG. 11 depicts a graphical representation using the visualization and analysis tool of the 24 hour period plot of FIGS. 8-10, including statistics relating to carbohydrate intake.

FIGS. 9-11 depict various features for obtaining statistics concerning CGM excursions and activity events. According to FIG. 9, a portion of the CGM data, arrow 851, is seen to exceed the upper shaded limit of 180 mg/dl. By hovering with a cursor over the portion of the CGM data that exceeds the limit (or alternatively by clicking in its region), the visualization tool is configured to provide a statistics box 850 that is superimposed onto the displayed plot 800. The statistics box 850 provides a snapshot summary of the duration of the excursion, the range of time of the excursion, as well as the maximum level of glucose and corresponding time stamp.

With reference to FIG. 10, a portion of the graphical representation (see arrow 853) is clearly below the lower limit of 70 mg/dl (below the center shaded area 808 of the top plot 800). In this instance and by hovering with a cursor over the portion 853 of the CGM data that is below the limit (or alternatively by clicking in its region), the visualization tool similarly provides a statistics box 854 superimposed onto the displayed plot 800. The statistics box 854 according to this version provides a snapshot summary of the duration of the excursion, the range of time of the duration, as well as the minimum level of glucose and corresponding time stamp.

In like manner and referring to FIG. 11, otherwise containing the same upper and lower plots 800, 840, a cursor can be hovered over a carbohydrate intake 856, such as at 18:00 on the top plot 800 to reveal a statistics box 855 that includes the time of day of the intake as well as the amount of carbohydrates taken. Each of the statistics boxes 850, 854, 855 can be provided in a manner to improve visibility, such as through color coding. It should be noted that each of the displayed data can similarly by provided in color and shading in order to suitably contrast any of the data from other data incorporated by the visualization tool.

Figure 12:
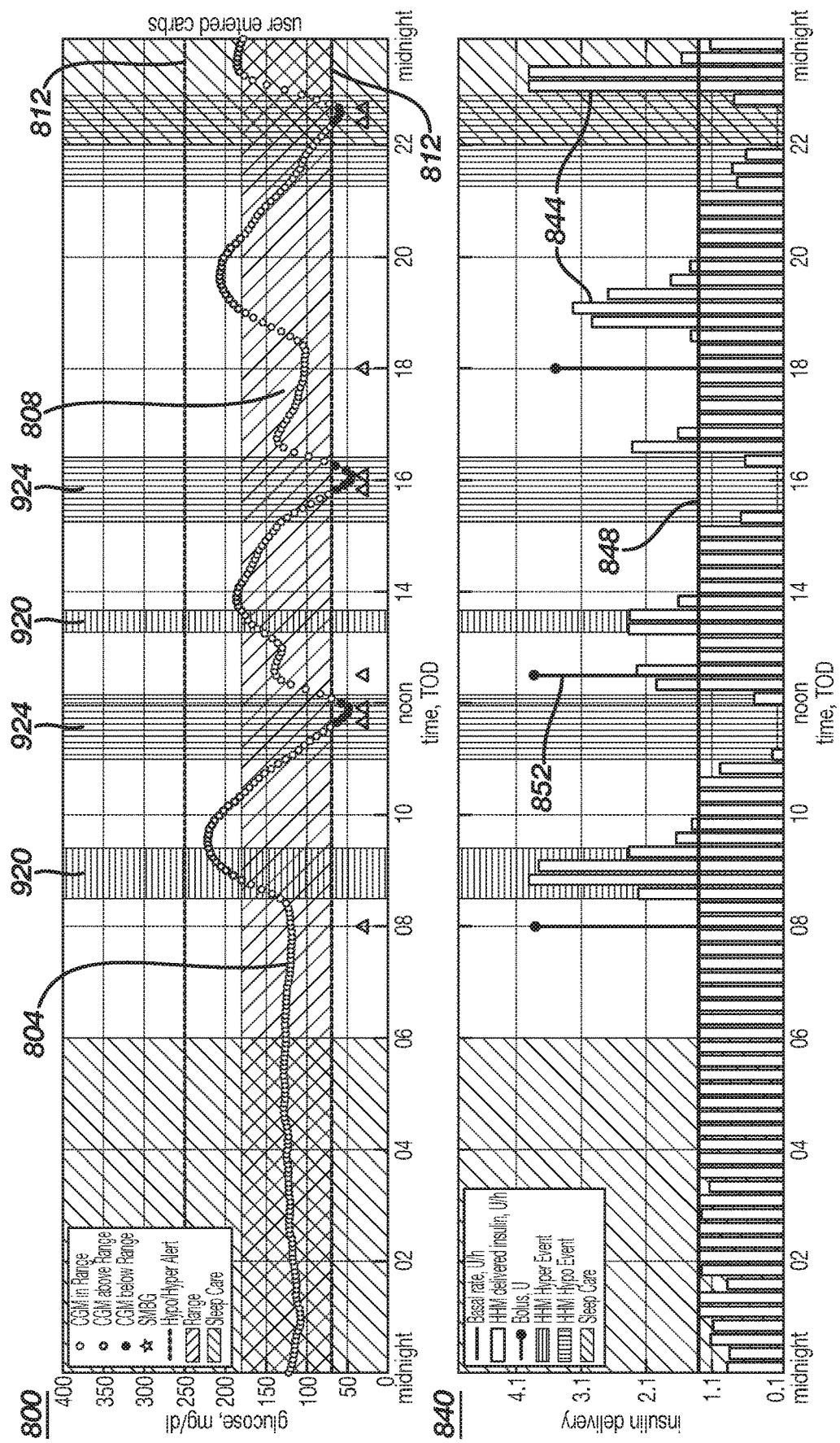
FIG. 12 depicts the graphical representation using the visualization and analysis tool of the 24 period plot of FIG. 8, with depicted APAEs being highlighted and coded based on whether Hypo- and Hyper-APAEs are present.
Figure 13:
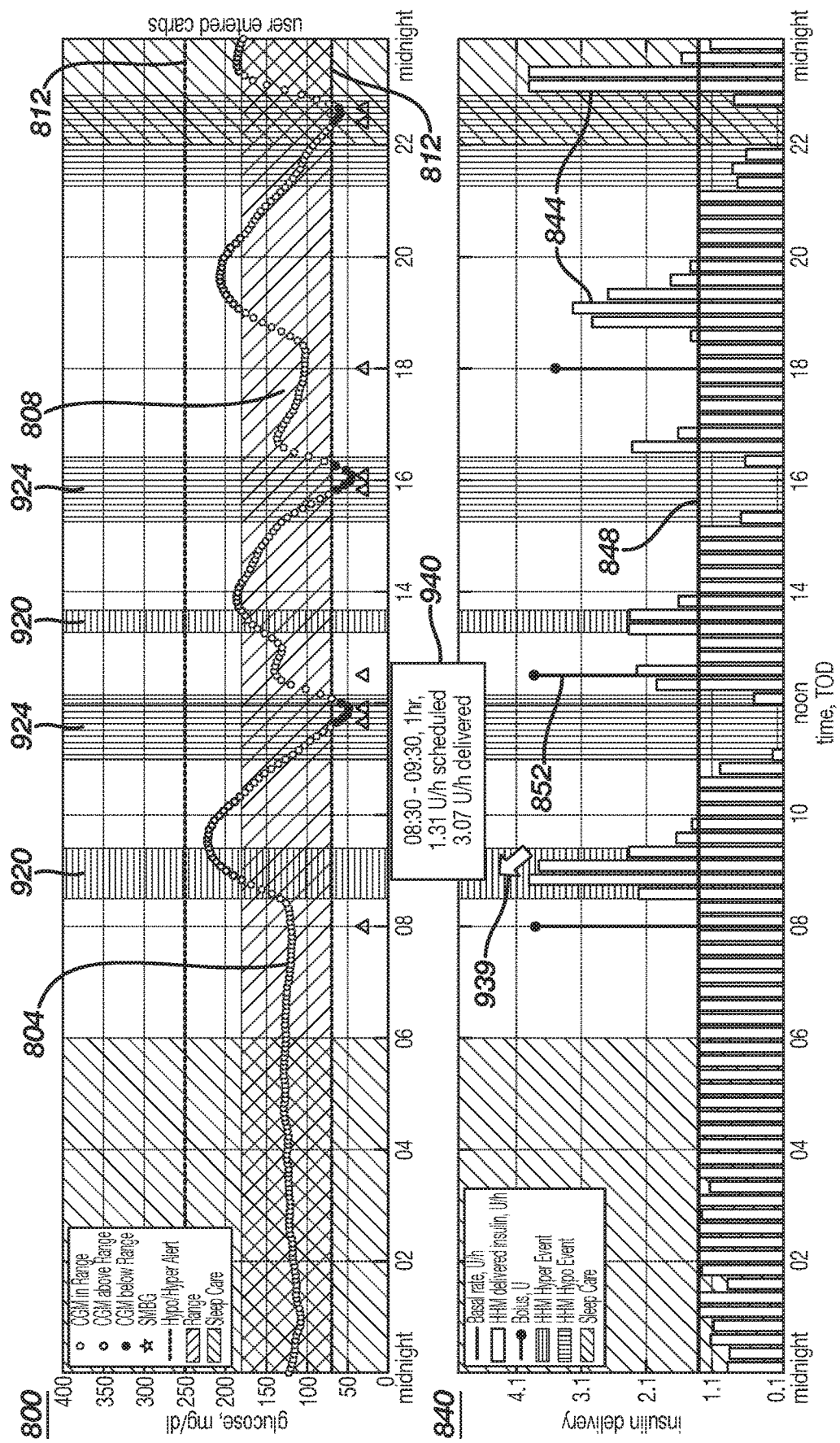
FIGS. 13 and 14 depict the graphical representation using the visualization and analysis tool of the 24 hour period plot of FIG. 12, in which statistics relating to highlighted Hyper-APAE and Hypo-APAE events, respectively, as displayed.
Figure 14:
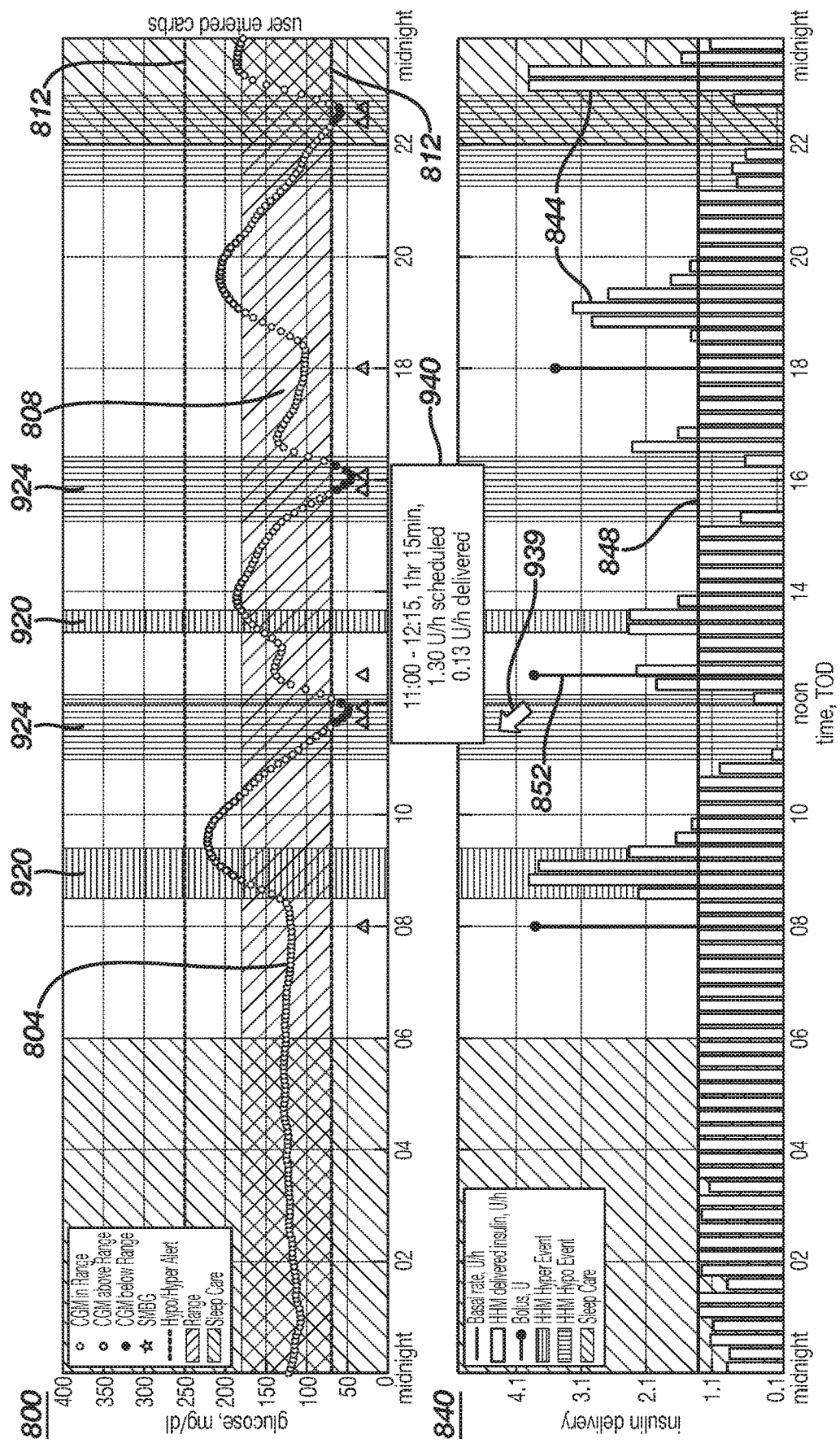

With reference to FIGS. 12-14, further enhancements relating to the dataset shown graphically in FIGS. 8-11 are herein described, based on the prior APAE metrics (Hypo- and Hyper-APAEs) discussed. According to FIG. 12, detected APAEs are provided in horizontal shaded areas 920, 924 that are preferably color coded depending on whether a Hypo-APAE or Hyper-APAE is detected and logged based on two consecutive 15 minute averages satisfying the defined conditions, as previously discussed and depicted in each of the top and bottom plots 800, 840.

With reference to FIGS. 13 and 14, the visualization and analysis tool permits the user to obtain additional statistical information pertaining to the detected APAE. According to one version and referring to FIG. 13 the cursor, see arrow 939 can be hovered over a detected and logged Hyper-APAE, as presented in the bottom (insulin delivery) plot 840 or alternatively by clicking in its shaded region 920, a statistics box 940 for that event is superimposed onto the display, preferably in contrasting color. The statistics box according to this version includes the duration of the Hyper-APAE event as well as the time of day of its occurrence, the average scheduled basal rate over that period, and the average system delivery rate over that period. In like manner and as shown in FIG. 14, any shaded Hypo-APAE can be further detailed by hovering the cursor, see arrow 943 over the Hypo-APAE (as shaded area 920 in the bottom plot 840), revealing a statistics box 944, preferably in contrasting color from that of the Hyper-APAE in which the statistics box includes the duration of the Hypo-APAE as well as the time of day of its occurrence, the average scheduled basal rate over that period and the average system delivery rate over that period. As previously noted, the onset of a Hypo- or Hyper APAE can occur while the CGM data indicates that the patient's insulin is still within the acceptable range, shown in the center shaded region. For example at 11:00, signifying the onset of the detected Hypo-APAE, the measured CGM data is still well within the acceptable 70-180 mg/dl range. The foregoing visualization provides confidence and trust to caregivers and users in the delivery (e.g., HHM) system.

Figure 15:
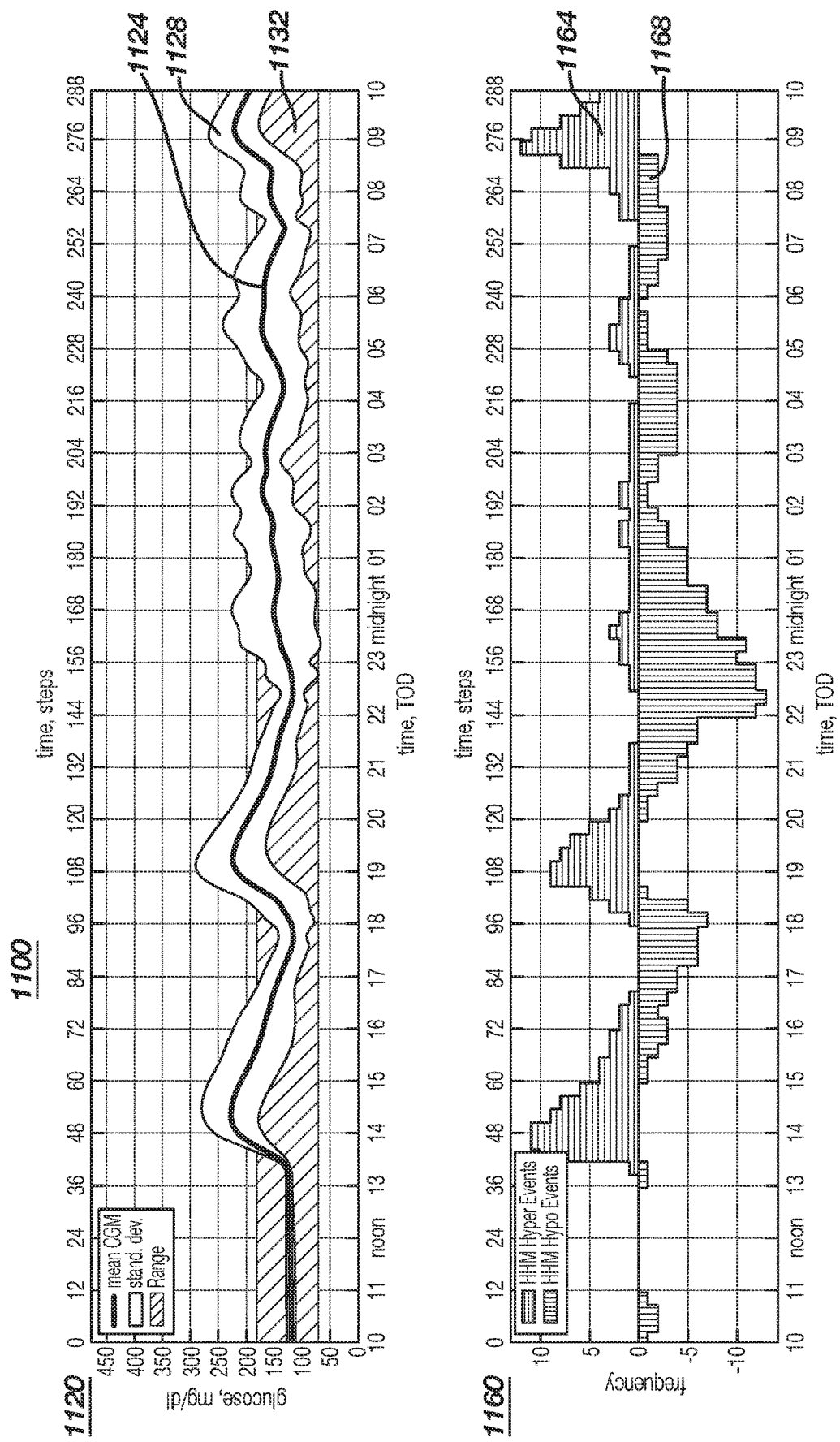
FIG. 15 represents a graphical depiction of an APAE landscape plot based upon two weeks of patient data, showing average CGM data as aligned with accumulated APAEs over that period.

The system's insulin adjusting activity and the use of the APAE metric enables a meaningful analysis of the system's operation. The amount of information, however, that can be generated can become overwhelming. In order to more effectively put this information to use and with reference to FIGS. 15 and 16, the visualization and analysis tool can create a landscape plot, which assesses the competencies of the delivery system over an extended period of time (e.g., 2 weeks) or any other period that is chosen by the patient or the health care professional. This tool permits a review of the system's action that is aligned with the time of day over the total extended period, thereby helping patients and health care professionals to fine-tune the patient's pump settings, such as basal rates, or carbohydrate intakes, to further improve glucose control. FIG. 15 details an exemplary landscape plot 1100 based upon two (2) weeks of data obtained from a patient compressed into a single one (1 day) format. A pair of plots 1120, 1160 is provided. The uppermost (top) plot 1120 depicts an average CGM data trace 1124 in which glucose, measured in mg/dl, is plotted against the time of day across the two weeks of data. The top axis of the plot 1120 represents time as represented by the number of steps (12 steps per hour, 1 step each 5 minutes) and in which the mean CGM is represented by the darkened curve 1124, and the shaded portion 1128 tracking the mean CGM represents a statistically significant range (i.e., one standard deviation) with the target range (70 mg/dl-180 mg/dl) being further shown in contrasting fashion, such as using different colors, shading or the like. In this particular instance, the target range is also shown as a shaded region 1132.

The bottommost (lower) plot 1160 is aligned with the upper plot 1120 and illustrates the number (frequency) of Hypo-APAEs and Hyper-APAEs (events) occurring over the same two week period. For purposes of this specific example, Hyper-APAEs 1164 are shown on the upper (positive) side of the plot and Hypo-APAEs 1168 are depicted on the bottom (negative) side, each being shown by shaded areas. Since the plot 1160 involves a total of 14 days, the maximum number of activity events 1164, 1168 for a time of day is also 14.

Figure 16:
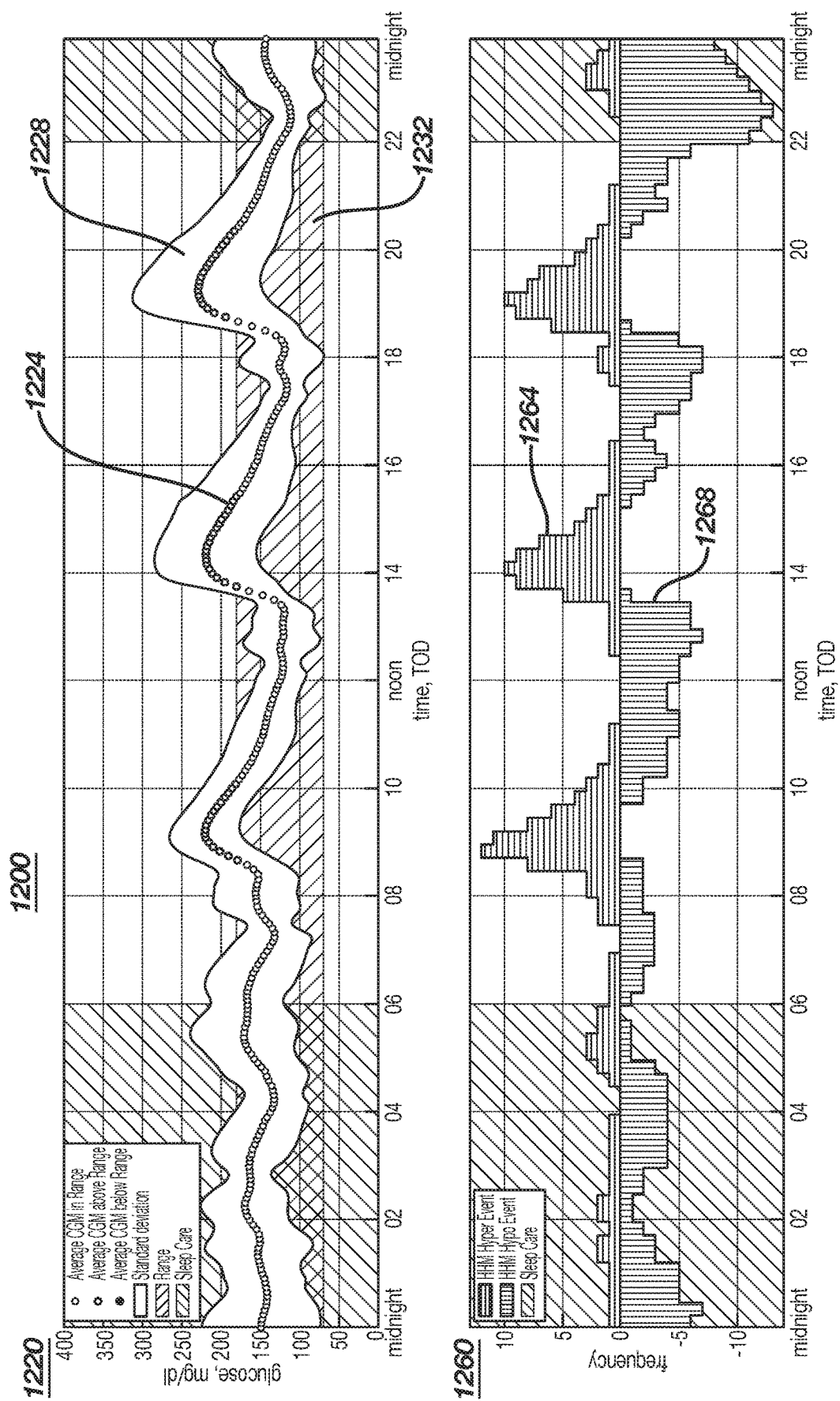
FIG. 16 depicts another graphical representation of another APAE landscape plot, showing average CGM data as aligned with accumulated APAEs.

FIG. 16 illustrates a landscape plots in accordance with another set of data taken over an extended (14 day) period, in which trends can easily be detailed and discerned by the patient and the health care professional. As in the prior example, a pair of plots 1220 and 1260 is provided, the top plot 1220 providing mean CGM (sensor) data over the extended period as represented by trace 1224 and a shaded portion 1228 indicating a statistically significant range (i.e., one standard deviation), the plot further defining a target range, also shown as a shaded portion 1232. The bottom plot 1260 depicts the frequency of Hypo-APAEs and Hyper-APAEs as aligned over the same period of time, with the Hyper-APAEs shown as shaded areas 1264 and Hypo-APAEs shown as shaded areas 1268. The use of activity event (e.g., APAE) metrics enables large amounts of information concerning the efficacy of the delivery system to be viewed all at once, and enabling the patient to better manage diabetic care. For example, and according to the bottom plot 1160 of FIG. 15, more than 10 Hypo-APAEs are consistently noted between 22:00 and 23:00, thereby leading to the conclusion that the basal rate could be adjusted during that period in order to improve the patient's overall glycemic condition.

The format of information presented can be suitably varied. For example and as shown in FIGS. 17-20, the tool can present system related data, including sensor data, insulin delivery data and detected activity events (APAEs) in a tabular format covering a selected predetermined time frame (e.g., single day, past three days, past seven days, past 14 days, past month, or a customized range) that a clinician, health care provider or the patient can select when accessing the tool.

For example, the tabular data can present overall control displaying the percentage of time the patient's glucose level is within an acceptable range (e.g., 70-180 mg/dL), as well as the mean glucose level over that time period. In addition, data relating to the state of the patient being either hypoglycemic—for example, the percentage of time the glucose level was below 50 mg/dL, below 60 mg/dL, or below 70 mg/dL—or hyperglycemic—for example, the percentage of time the glucose level was above 180 mg/dL, above 250 mg/dL, or above 300 mg/dL—can be tabularly presented. A sample table having this data is depicted in FIG. 17. In addition, this data can further be presented as an average total daily dose (TDD) of insulin, as well as basal-bolus ratio for a designated time period (e.g., one day). An example of the foregoing table is depicted in FIG. 18.

The data presented can further include the number of activity events (i.e., APAEs (whether hypo or hyper, as previously discussed) that have occurred during a specified time period. With regard to activity events, the tabular data can further include more specific data including the length of time the activity event(s) occurred, the total amount of basal insulin withheld (hypo-APAE) or delivered (hyper-APAE) during the event, the sensor (CGM) determined nadir (hypo-APAE) or peak (hyper-APAE), the sensor determined value at the initiation of the activity event and the end of the activity event and other pertinent data. A sample table including this latter data is depicted in FIG. 19 for hypo-related activity events and FIG. 20 for hyper-related activity events, each being determined in accordance with the protocol and based on periodic insulin delivery (e.g., 5 minutes, 12 deliveries per hour) and CGM monitoring.

It will be readily apparent that other modifications and variations are possible within the inventive ambits which have been described herein and as recited according to the following claims:

The invention claimed is:

1. An insulin delivery system comprising:
    a pump that is controllable to adjust insulin delivery relative to a baseline delivery rate;
    a sensor for measuring glucose levels of the patient;
    a controller coupled to the pump and sensor and configured to calculate insulin delivery based upon an autonomous modulation algorithm utilizing measured signals from the pump and sensor and configured to perform sequential averaging of insulin deliveries made by the system and a scheduled basal rate over a period of time; and
    a visualization and analysis tool engageable with the controller, the tool enabling the detection and display of at least one activity event in which the controller compares a scheduled insulin delivery to actual delivery of insulin by the system and determines the presence of the at least one activity event based on periodic sample averaging of both the scheduled and delivered insulin and wherein the at least one activity event is based on a ratio of a system-delivered insulin amount to the corresponding scheduled amount being less than or greater than a therapeutically relevant ratio.

2. The delivery system as recited in claim 1, wherein the at least one activity event is designated as either a hypoglycemic activity event when the ratio of system delivered insulin to the corresponding scheduled amount is less than the therapeutically relevant ratio or a hyperglycemic activity event when the ratio of system-delivered insulin amount is greater than the therapeutically relevant ratio.

3. The delivery system as recited in claim 1, wherein the visualization and analysis tool creates a plot based over an extended period of time in which the frequency of detected activity events is displayed based on the time of day over the extended period of time.

4. The delivery system as recited in claim 3, in which the extended period of time is greater than one week.

5. The delivery system as recited in claim 3, in which the extended period of time is greater than two weeks.

6. The delivery system as recited in claim 3, wherein the extended period of time is selectable.

7. The delivery system as recited in claim 1, in which the delivery of insulin by the controller is governed by model predictive control.

8. The delivery system as recited in claim 1, in which system data is displayed by the tool in at least one tabular format.

9. The delivery system as recited in claim 1, in which the at least one activity event can occur even while glucose levels of a patient as detected by the sensor are still within an acceptable target range.

* * * * *